(12) United States Patent
Yoshikawa et al.

(10) Patent No.: US 7,568,378 B2
(45) Date of Patent: Aug. 4, 2009

(54) SENSOR

(75) Inventors: Kumiko Yoshikawa, Kasugai (JP); Makoto Kume, Inuyama (JP); Noboru Matsui, Iwakura (JP); Tomohiro Nakamura, Konan (JP)

(73) Assignee: NGK Spark Plug Co., Ltd., Aichi (JP)

( * ) Notice: Subject to any disclaimer, the term of this patent is extended or adjusted under 35 U.S.C. 154(b) by 20 days.

(21) Appl. No.: 12/013,491

(22) Filed: Jan. 14, 2008

(65) Prior Publication Data

US 2008/0173069 A1 Jul. 24, 2008

(30) Foreign Application Priority Data

Jan. 15, 2007 (JP) .............................. 2007-006329
Dec. 4, 2007 (JP) .............................. 2007-313680

(51) Int. Cl.
*G01N 9/00* (2006.01)

(52) U.S. Cl. .................................................... 73/31.05

(58) Field of Classification Search ................. 73/31.05
See application file for complete search history.

(56) References Cited

U.S. PATENT DOCUMENTS

| 7,032,433 | B2* | 4/2006 | Hayashi et al. ............ 73/31.05 |
| 7,340,942 | B2* | 3/2008 | Matsuo et al. ............. 73/31.05 |
| 7,398,673 | B2* | 7/2008 | Nishio et al. ............... 73/31.05 |
| 7,415,877 | B2* | 8/2008 | Okumura et al. ............. 73/431 |
| 7,430,894 | B2* | 10/2008 | Matsuo et al. ............. 73/31.05 |
| 2007/0052862 | A1 | 3/2007 | Matsuo et al. |
| 2007/0096615 | A1 | 5/2007 | Matsuo et al. |
| 2007/0119235 | A1 | 5/2007 | Matsuo et al. |
| 2007/0243760 | A1 | 10/2007 | Fujita et al. |

FOREIGN PATENT DOCUMENTS

| WO | 2005029057 A1 | 3/2005 |
| WO | 2005029058 A1 | 3/2005 |
| WO | WO 2005029057 | 3/2005 |
| WO | WO 2005029058 | 3/2005 |

* cited by examiner

*Primary Examiner*—Hezron Williams
*Assistant Examiner*—Rodney T Frank
(74) *Attorney, Agent, or Firm*—Sughrue Mion, PLLC

(57) ABSTRACT

A sensor including: a detecting element (4) as defined herein; a plurality of metallic terminal members (10, 211, 221, 231, 268) as defined herein; and an insulating separator (82) as defined herein, wherein the insulating separator includes: an outer separator (183) which surrounds the electrode terminal portions of the detecting element and the metallic terminal members; and an inner separator (185, 285) at least a portion of which is disposed radially inwardly of the outer separator and which has partition walls (187, 190, 191, 287, 290, 291) for positioning the plurality of metallic terminal members and insulating the plurality of metallic terminal members from one another.

14 Claims, 22 Drawing Sheets

1ST STATE (1ST STEP)  2ND STATE (2ND STEP)  3RD STATE (3RD STEP)

SENSOR

BACKGROUND OF THE INVENTION

1. Field of the Invention

The present invention relates to a sensor including a detecting element having a plate-type shape extending in an axial direction and having electrode terminal portions formed on its rear end side, a plurality of metallic terminal members respectively connected to the electrode terminal portions of the detecting element, and an insulating separator surrounding at least a portion of the detecting element and the metallic terminal members and which causes the electrode terminal portions of the detecting element and the metallic terminal members to come into contact with one another.

2. Description of the Related Art

A sensor having a detecting element, metallic terminal members, and an insulating separator is known as a conventional sensor.

The insulating separator surrounds at least a portion of the detecting element and the metallic terminal members, and is adapted to cause the electrode terminal portions of the detecting element and the metallic terminal members to come into contact with one another inside the insulating separator.

A sensor has been proposed in which boundary portions (87, 89) are provided inside the insulating separator so that the metallic terminal members do not come into contact with one another in arranging the plurality of metallic terminal members in the insulating separator (refer to International Publication No. 2005/029057 (see FIGS. 1, 4, and 5) (corresponding to US2007/0052862A1)).

3. Problems to be Solved by the Invention

However, as the number of metallic terminal members increases in conjunction with the trend toward higher performance of the detecting element, a region available for suitably arranging respective metallic terminal members in the insulating separator is decreased.

Namely, since the boundary portions provided inside the insulating separator define a narrow region, it is difficult to directly view the interior state of the insulating separator. Consequently, it is difficult to confirm whether or not the metallic terminal members retain their original arrangement.

In addition, in a case where the insulating separator includes an element insertion hole penetrating in an axial direction, there are cases where a metallic terminal member which has already been arranged in the element insertion hole hinders the inserting operation of a metallic terminal member which is inserted at a later time. This problem becomes more apparent as the number of metallic terminal members increases.

For these reasons, if the number of metallic terminal members increases, the possibility of the metallic terminal members being arranged at misaligned positions in the insulating separator becomes high. If the metallic terminal members are misaligned, the connection between the metallic terminal member and the detecting element (specifically, an electrode terminal portion) possibly becomes faulty, making it impossible to properly output a detection signal (sensor signal) from the detecting element to an external device or the like.

Accordingly, the present invention has been made in view of the above-described problems, and an object thereof is to provide a sensor having an insulating separator which allows for easy arrangement of metallic terminal members at predetermined positions.

SUMMARY OF THE INVENTION

The above object has been achieved in accordance with a first aspect of the invention by providing a sensor comprising: a detecting element having a plate-like shape extending in an axial direction and whose leading end side is directed toward a gas to be measured, and a plurality of electrode terminal portions formed on at least one of an obverse plate surface and a reverse plate surface of a rear end side of the detecting element; a plurality of metallic terminal members for electrically connecting an external device and the electrode terminal portions of the detecting element; and an insulating separator in which the electrode terminal portions of the detecting element and the metallic terminal members are connected with one another, wherein the insulating separator comprises: an outer separator which surrounds the electrode terminal portions of the detecting element and the metallic terminal members; and an inner separator at least a portion of which is disposed radially inwardly of the outer separator and which has partition walls for positioning respective ones of the plurality of metallic terminal members and for insulating the plurality of metallic terminal members from one another.

This sensor is characterized in that the insulating separator is constituted not by a single member, but by a plurality of members including an outer separator and an inner separator.

Namely, the insulating separator is not configured with partition walls fixed to the interior of the insulating separator, but rather is configured such that the partition walls are formed on the inner separator which is separate from the outer separator.

By using such an insulating separator, with respect to the metallic terminal members whose positioning in the insulating separator is difficult, the metallic terminal members together with the inner separator are inserted into the outer separator. In this manner it is possible to arrange the metallic terminal members at appropriate positions of the insulating separator.

Namely, in a preliminary stage before inserting the metallic terminal member into the insulating separator, the metallic terminal member is arranged on the inner separator which is a part of the insulating separator, so that the relative position between the inner separator and the metallic terminal member can be set in a manner that is directly visually confirmable. Since the relative position between the inner separator and the metallic terminal member can thus be directly visually confirmed, the relative position between the inner separator and the metallic terminal member can easily be set to a particular position.

As a result, when the metallic terminal member together with the inner separator is inserted into the outer separator, the relative position between the inner separator and the outer separator can be easily set to a particular position, and the operation of positioning the metallic terminal member in the insulating separator (outer separator) is facilitated.

Hence, according to the invention, even in the sensor provided with the insulating separator, the metallic terminal members can easily be arranged at appropriate positions in arranging the metallic terminal members in the insulating separator.

It should be noted that the sensor in accordance with the invention is not limited to the form in which the metallic terminal members are inserted into the outer separator after all of the plurality of metallic terminal members are arranged on the inner separator. An arrangement may be provided such that after one or some of the plurality of metallic terminal members are arranged on the inner separator and are inserted into the outer separator, the remaining metallic terminal members are subsequently arranged in the outer separator.

In addition, the electrode terminal portions which are formed on the obverse plate surface and the reverse plate surface of the detecting element are not limited to those in which a plurality of electrode terminal portions are formed on the obverse plate surface and the reverse plate surface, respectively. It is possible to adopt a form in which a plurality of obverse plate surfaces (or reverse plate surfaces) are formed, and a single reverse plate surface (or obverse plate surface) is formed.

Furthermore, the outer separator is not limited to a single member, and it is possible to adopt an outer separator having a plurality of members which sandwich the detecting element and the metallic terminal members.

For example, in the above-described sensor, in accordance with a second aspect of the invention, the outer separator has a cylindrical shape and has an element insertion hole penetrating therethrough in the axial direction, and at least a portion of the inner separator is disposed inside the element insertion hole.

Namely, even in the case where the outer separator is used which is formed by a single member and has an element insertion hole, with respect to the metallic terminal members whose positioning in the element insertion hole is difficult, the metallic terminal members together with the inner separator are inserted into the element insertion hole of the outer separator. Consequently, it is possible to arrange the metallic terminal members at predetermined positions of the element insertion hole.

Next, in the above-described sensor, in accordance with a third aspect of the invention, at least one of the plurality of metallic terminal members has a projecting portion projecting perpendicularly to the axial direction, and at least one of the partition walls abuts against the projecting portion to effect positioning of the metallic terminal member in the axial direction.

By adopting a configuration in which the metallic terminal member has the projecting portion, and the partition wall of the inner separator abuts against the projecting portion to effect axial positioning of the metallic terminal member, when the metallic terminal member tends to move in the axial direction (in the direction toward the rear end or the leading end), the partition wall abuts against the projecting portion of the metallic terminal member, thereby making it possible to limit the moving range of the metallic terminal member.

As a result, the axial positioning of the metallic terminal member with respect to the inner separator is facilitated, and it is possible to suppress the occurrence of an offset in the relative axial position between the metallic terminal member and the inner separator.

Therefore, according to the invention, in arranging the metallic terminal members in the element insertion hole of the insulating separator, the problem encountered in the operation of relatively positioning the inner separator and the metallic terminal member is alleviated, so that it becomes possible to easily arrange the metallic terminal member at a predetermined position.

It should be noted that the projecting portion provided on the metallic terminal member may be singular or plural.

Next, in the above-described sensor, in accordance with a fourth aspect of the invention, the metallic terminal member has a surrounded region surrounded by the insulating separator, and the projecting portion is provided closer to a leading end side than an axially central position of the surrounded region.

Since the projecting portion and the partition wall abut each other by means of a metallic terminal member in which the position where the projecting portion is specified, the positioning of the leading end side of the surrounded region of the metallic terminal member is facilitated.

When the outer separator having the element insertion hole is used, there are cases where after the metallic terminal member together with the inner separator are arranged in the element insertion hole, the operation of inserting the detecting element from the leading end side of the element insertion hole is carried out. In such a case, by using the metallic terminal member in which the projecting portion is formed closer to the leading end side than the axially central position of the surrounded region, even if an external force is applied to the metallic terminal member accompanying the inserting operation of the detecting element, it is possible to suppress movement of the metallic terminal member to an inappropriate position.

Next, in the above-described sensor, in accordance with a fifth aspect of the invention, at least one of the plurality of metallic terminal members has a leading end engaging portion which engages a leading end face of the insulating separator.

Thus, since the metallic terminal member has a leading end engaging portion, it becomes possible to easily determine the relative position between the leading end face of the insulating separator and the metallic terminal member, thereby facilitating the axial positioning between the metallic terminal member and the insulating separator. Particularly when the metallic terminal member is arranged in the insulating separator, the metallic terminal member is arranged so that the leading end engaging portion abuts the leading end face of the insulating separator, thereby making it possible to easily set the arrangement position of the metallic terminal member in the insulating separator to a particular position.

In addition, since the leading end engaging portion of the metallic terminal member engages the leading end face of the insulating separator, there is an advantage in that even in a case where a particular component element (e.g., a partition wall of a projecting shape) is not provided on the insulating separator, it is possible to determine the relative position between the metallic terminal member and the insulating separator.

As a result, in accordance with the invention, the accuracy of the arrangement position of the metallic terminal member in the insulating separator can be determined by observing whether or not the leading end engaging portion abuts against the leading end face of the insulating separator. Therefore, the operation of positioning the insulating separator relative to the metallic terminal member is further facilitated.

The portion of the leading end face of the insulating separator with which the leading end engaging portion of the metallic terminal member engages may be either the leading end face of the outer separator or the leading end face of the inner separator, or may be both leading end faces of the outer separator and the inner separator.

Next, in the above-described sensor, in accordance with a sixth aspect of the invention, at least one of the plurality of metallic terminal members has a frame body portion of an elongated shape extending in the axial direction and an element abutting portion which extends from a leading end side of the frame body portion such that at least a portion thereof is disposed between the frame body portion and the detecting element, and which element abutting portion abuts against an electrode terminal portion of the detecting element, and wherein the inner separator has a plate-shaped body portion adapted to abut against the frame body portion.

In other words, since the inner separator has the plate-shaped body portion, even in the metallic terminal member having the frame body portion and the element abutting portion, the arrangement position of the metallic terminal member relative to the inner separator can be easily set to a particular position in the preliminary stage before arranging the metallic terminal member into the outer separator. This facilitates the operation of positioning the metallic terminal members in the insulating separator.

Next, in the above-described sensor provided with the metallic terminal member having the frame body portion and the element abutting portion, in accordance with a seventh aspect of the invention, the element abutting portion has a connecting portion which is connected to a leading end of the frame body portion, and at least a portion of the connecting portion is adapted to undergo elastic deformation upon application of an external force thereto by the detecting element.

When the detecting element is disposed with the metallic terminal members arranged in the insulating separator, the metallic terminal member having such a connecting portion is able to reliably come into contact with the detecting element as the connecting portion is elastically deformed, so that the contact state with the detecting element becomes excellent.

In addition, when the outer separator has an element insertion hole, the metallic terminal member having such a connecting portion is able to absorb the external force from the detecting element as the connecting portion is elastically deformed at the time of inserting the detecting element into the element insertion hole with the metallic terminal members arranged therein. Consequently, when the detecting element is inserted into the element insertion hole, it is possible to prevent the arrangement position of the metallic terminal member from moving due to the external force from the detecting element.

Next, in the above-described sensor, in accordance with an eighth aspect of the invention, the outer separator has a recessed portion for receiving the plate-shaped body portion of the inner separator, and the plate-shaped body portion of the inner separator is disposed in the recessed portion by sliding from a leading end side of the outer separator toward a rear end side along an inner surface of the insulating separator.

Since the outer separator is provided with the recessed portion, when the inner separator is arranged in the outer separator, it is possible to easily set the arrangement position of the inner separators in the outer separator. By using an outer separator having such a configuration, the operation of positioning the metallic terminal members in the insulating separator is further facilitated.

In addition, when the outer separator has an element insertion hole, since the outer separator is provided with the recessed portion, when the inner separator is inserted (slid) into the element insertion hole of the outer separator, it is possible to easily set the arrangement position of the inner separator in the element insertion hole.

Next, in the above-described sensor, in accordance with a ninth aspect of the invention, the outer separator has on a rear end side of the recessed portion a position determining portion which effects positioning of the inner separator in the axial direction inside the outer separator by abutting against the plate-shaped body portion of the inner separator.

In other words, since the outer separator is provided with the position determining portion, the outer separator is capable of limiting the sliding range (specifically, the sliding range in the direction toward the rear end) of the inner separator inside the outer separator. Further, the position where the position determining portion is formed is set in advance so that the position where the inner separator is arranged in the outer separator coincides with a target position, and a rear opposing face of the inner separator (plate-shaped body portion) abuts against the position determining portion when the inner separator is arranged in the outer separator. Consequently, the positioning operation at the time of arranging the inner separator in the outer separator is facilitated.

Thus, since the positioning operation at the time of arranging the inner separator in the outer separator is facilitated, it is possible to alleviate the trouble encountered in the positioning operation when the metallic terminal members and the inner separators are arranged in the outer separator, thereby facilitating positioning the metallic terminal members in the outer separator.

Therefore, according to the invention, in arranging the metallic terminal members in the insulating separator, it becomes possible to easily arrange the metallic terminal members at predetermined positions.

The "rear opposing face" is a surface facing the rear end side, such as the rearmost end portion of the inner separator. However, the rear opposing face of the inner separator in the invention is not limited to the rearmost end portion of the inner separator. For instance, a projecting portion may be formed on the leading end side of the inner separator, and a surface of the projecting portion facing the rear side may be a rear opposing face.

In addition, the sensor in which the position determining portion of the outer separator and the partition walls of the inner separator are jointly formed has an advantage in that, concerning the metallic terminal members, the inner separator, and the outer separator, their respective axial relative positions can be positioned more easily.

Next, in the above-described sensor, in accordance with a 10th aspect of the invention, of the plurality of electrode terminal portions, two adjacent ones of the electrode terminal portions in a same plane of the detecting element are formed at different axial positions, and the individual ones of plurality of metallic terminal members are arranged so as to connect to corresponding ones of the electrode terminal portions.

In such a configuration, it is possible to secure a large distance between two adjacent ones of the electrode terminal portions and secure a large distance also between the two metallic terminal members which are connected to these two electrode terminal portions. Hence, it is possible to ensure insulation between two adjacent ones of the electrode terminal portions and to secure insulation between the two metallic terminal members which are connected to these electrode terminal portions.

In a sensor having such a configuration, as for the plurality of metallic terminal members, their respective axial arrangement positions are set in correspondence with the forming positions of the electrode terminal portions which the metallic terminal members are to be connected to. Incidentally, the number of the inner separators provided in one insulating separator is not limited to a singular member, and a plurality of inner separators may be provided in one insulating separator.

Accordingly, in the above-described sensor, in accordance with an 11th aspect of the invention, the detecting element has a plurality of electrode terminal portions formed on an obverse plate surface and a reverse plate surface, respectively, on the rear end side, and a pair of inner separators are provided as the inner separator and are respectively arranged on the obverse plate surface and the reverse plate surface of the detecting element.

Thus, where a plurality of electrode terminal portions are formed on the obverse plate surface and the reverse plate surface, respectively, of the detecting element, a pair of inner separators are provided so that the metallic terminal members can be appropriately arranged on both of the obverse plate surface and the reverse plate surface between the plate surfaces of the detecting element. This is even the case where metallic terminal members whose arrangement is difficult are present.

Further, in the above-described sensor having the detecting element in which a plurality of electrode terminal portions are formed on the obverse plate surface and the reverse plate surface, respectively, in accordance with a 12th aspect of the invention, the plurality of electrode terminal portions, the electrode terminal portions which are formed on the obverse plate surface of the detecting element and the electrode terminal portions which are formed on the reverse plate surface of the detecting element are arranged plane-symmetrically about the detecting element.

Thus, in the case where the plurality of electrode terminal portions are formed on the obverse plate surface and the reverse plate surface of the detecting element plane-symmetrically about the detecting element, the plurality of metallic terminal members are also arranged substantially plane-symmetrically. As a result, the distribution of pressure applied from the plurality of metallic terminal members to the detecting element becomes substantially similar on the obverse plate surface and the reverse plate surface of the detecting element.

Consequently, it becomes possible to prevent contact between the detecting element and the plurality of metallic terminal members from becoming nonuniform between the obverse plate surface and the reverse plate surface of the detecting element, and render satisfactory the state of contact between each metallic terminal member and a corresponding electrode terminal portion.

Next, in accordance with a 13th aspect, the present invention provides a sensor comprising: a detecting element which has a plate-like shape extending in an axial direction and whose leading end side is directed toward a gas to be measured, and a plurality of electrode terminal portions formed on at least one of an obverse plate surface and a reverse plate surface of a rear end side of the detecting element; a plurality of metallic terminal members for electrically connecting to an external device and the electrode terminal portions of the detecting element; and an insulating separator which in which the electrode terminal portions of the detecting element and the metallic terminal members are connected with one another, wherein at least one of the plurality of metallic terminal members comprises a frame body portion of an elongated shape extending in the axial direction and an element abutting portion which extends from a leading end side of the frame body portion such that at least a portion thereof is disposed between the frame body portion and the detecting element, and which element abutting portion abuts against an electrode terminal portion of the detecting element, the element abutting portion having a connecting portion which is connected to a leading end of the frame body portion, and at least a portion of the connecting portion is adapted to undergo elastic deformation upon application of an external force thereto by the detecting element, wherein, of the plurality of electrode terminal portions, two adjacent ones of the electrode terminal portions in a same plane of the detecting element are formed at different axial positions, and wherein respective axial arrangement positions of the plurality of metallic terminal members are set in correspondence with the electrode terminal portions to which the metallic terminal members are connected.

In the sensor having the above-described configuration, it is possible to secure a large distance between two adjacent ones of the electrode terminal portions and also between the two metallic terminal members which are connected to these two electrode terminal portions. Hence, it is possible to ensure adequate insulation between two adjacent ones of the electrode terminal portions and between the two metallic terminal members which are connected to these electrode terminal portions.

Therefore, according to the invention, in the sensor provided with an insulating separator, since two adjacent ones of the metallic terminal members can be arranged in a state in which mutual insulation is secured, the metallic terminal members can be easily arranged at predetermined positions.

The electrode terminal portions which are formed on the obverse plate surface and the reverse plate surface of the detecting element are not limited to those in which a plurality of electrode terminal portions are formed on the obverse plate surface and the reverse plate surface, respectively. It is possible to adopt a form in which a plurality of obverse plate surfaces (or reverse plate surfaces) are formed, and a single reverse plate surface (or obverse plate surface) is formed.

Next, in the above-described sensor (in the 13th aspect), in accordance with a 14th aspect of the invention, the detecting element has a plurality of electrode terminal portions formed on an obverse plate surface and a reverse plate surface, respectively, on the rear end side, and, of the plurality of electrode terminal portions, the electrode terminal portions which are formed on the obverse plate surface of the detecting element and the electrode terminal portions which are formed on the reverse plate surface of the detecting element are arranged plane-symmetrically about the detecting element.

Thus, in the case where the plurality of electrode terminal portions are formed on the obverse plate surface and the reverse plate surface of the detecting element plane-symmetrically about the detecting element, the plurality of metallic terminal members are also arranged substantially plane-symmetrically. As a result, the state of distribution of pressure applied from the plurality of metallic terminal members to the detecting element becomes substantially similar on the obverse plate surface and the reverse plate surface of the detecting element.

Consequently, it becomes possible to prevent contact between the detecting element and the plurality of metallic terminal members from becoming nonuniform between the obverse plate surface and the reverse plate surface of the detecting element, and to render a satisfactory state of contact between individual ones of the metallic terminal member and a corresponding electrode terminal portion.

DESCRIPTION OF REFERENCE NUMERALS

Figure 1:
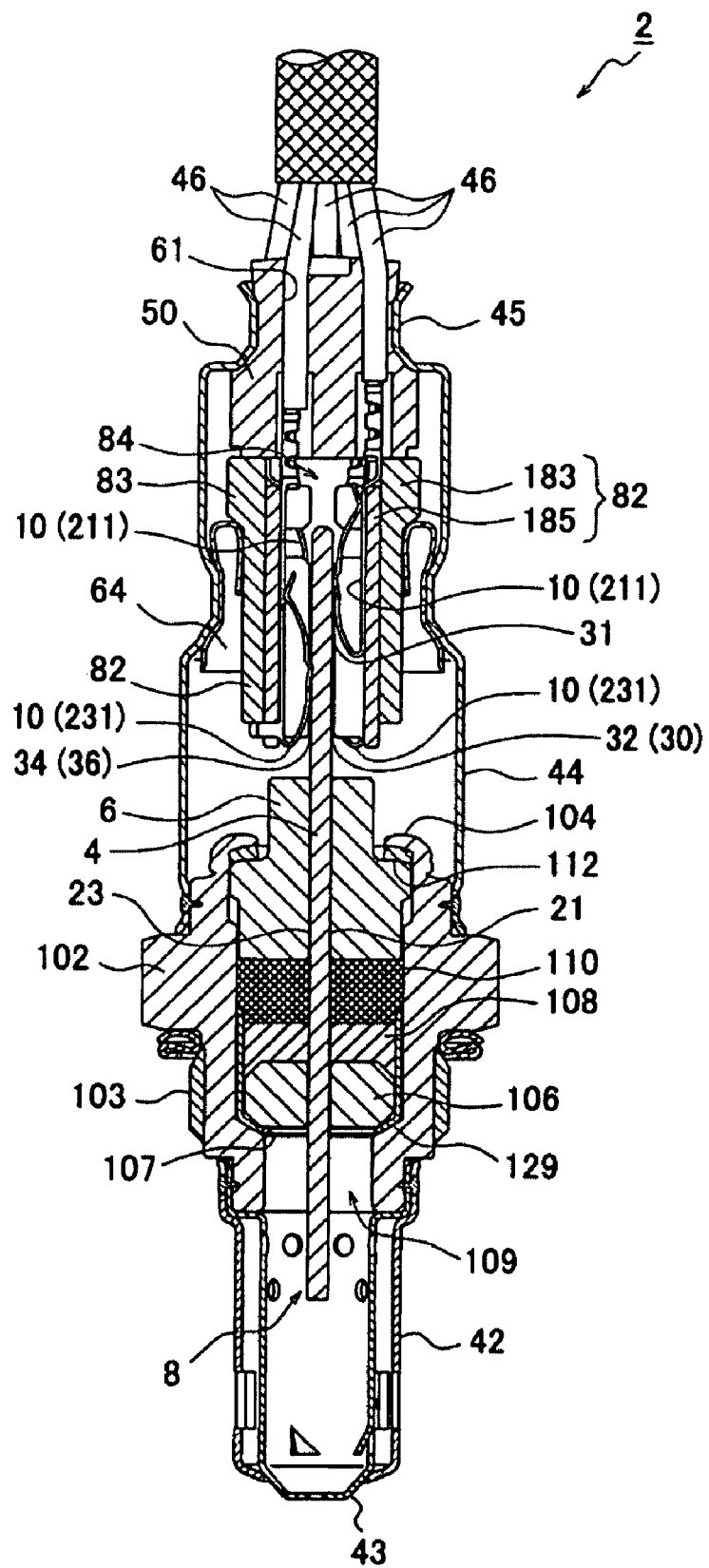
FIG. 1 is a cross-sectional view illustrating the overall configuration of a $NO_x$ sensor.

Reference numerals used to identify various structural features in the drawings include the following.

2: $NO_x$ sensor, 4: detecting element, 10: leadframe, 30, 31, 32, 33, 34, and 36: electrode terminal portions, 82: insulating separator, 84: element insertion hole, 86: frame arranging groove, 183: outer separator, 184: position determining portion, 185: inner separator, 186: plate-shaped body portion, 187: partition wall, 188: notched portion, 189: rear end portion, 190: rear end partition wall, 191: leading end partition wall, 192: rear-surface abutting portion, 193: side-surface abutting portion, 195: recessed portion, 211: first leadframe, 217: lead wire connecting portion, 219: frame retaining portion, 221: second leadframe, 231: third leadframe, 235: first retaining surface, 237: second retaining surface, 317: terminal fixing guide portion, 318: terminal retaining portion, 319: lead wire connecting portion

DETAILED DESCRIPTION OF THE INVENTION

Hereafter, a description will be given of an embodiment of the invention with reference to the accompanying drawings. However, the present invention should not be construed as being limited thereto.

In this embodiment, a description will be given of a $NO_x$ sensor 2 which is a type of gas sensor. The $NO_x$ sensor 2 has a detecting element (gas sensor element) incorporated therein for detecting a particular gas component in an exhaust gas subject to measurement, and is installed, for example, in an internal combustion engine.

FIG. 1 is a cross-sectional view illustrating the overall configuration of the $NO_x$ sensor 2.

The $NO_x$ sensor 2 is comprised of a cylindrical metal shell 102 having a threaded portion 103 formed on its outer surface for fixing to an exhaust pipe; a detecting element 4 formed in the shape of a plate and extending in an axial direction (in the vertical direction in the drawing); a cylindrical ceramic sleeve 6 which is disposed so as to surround the radial periphery of the detecting element 4; an insulating separator 82 having an element insertion hole 84 penetrating in the axial direction; and six leadframes 10 (only some are shown in FIG. 1) which are connected to the detecting element 4.

The detecting element 4 has a plate-like shape extending in the axial direction, and has a detecting portion 8 formed on its leading end side (a lower side in the drawing) which is directed toward the gas to be measured and is covered with a protective layer (not shown). Further, the detecting element 4 has electrode terminal portions 30, 31, 32, 34, 35 and 36 formed on a first plate surface 21 and a second plate surface 23 which assume the positional relationship of obverse and reverse sides in the outer surfaces of the rear end side (an upper side in the drawing).

The insulating separator 82 is formed of an insulating material, and has an element insertion hole 84 in which at least portions of the detecting element 4 and the leadframes 10 are provided. As the insulating separator 82 holds the leadframes 10 and the detecting element 4 inside the element insertion hole 84, the leadframes 10 are respectively electrically connected to the electrode terminal portions 30, 31, 32, 34, 35 and 36 of the detecting element 4. In addition, the leadframes 10 are also respectively connected to lead wires 46 disposed inside the sensor from the outside, and form current paths of electric current flowing between, on the one hand, an external device to which the lead wires 46 are connected and, on the other hand, the electrode terminal portions 30, 31, 32, 34, 35 and 36.

The metal shell 102 is configured substantially in the shape of a cylinder which has a through hole 109 penetrating therethrough in the axial direction and has a shelf portion 107 projecting radially inwardly of the through hole 109. In addition, the metal shell 102 is constructed so as to hold the detecting element 4 inserted in the through hole 109 in a state in which the detecting portion 8 is disposed outside the leading end side of the through hole 109, while the electrode terminal portions 30, 31, 32, 34, 35 and 36 are disposed outside the rear end side of the through hole 109. Further, the shelf portion 107 is formed as an inwardly oriented tapered surface inclined with respect to a plane perpendicular to the axial direction.

A ceramic holder 106 having an annular shape, powder filler layers 108 and 110 (hereafter, also referred to as talc rings 108 and 110), and the aforementioned ceramic sleeve 6 are stacked in that order from the leading end side toward the rear end side inside the through hole 109 of the metal shell 102 so as to surround the radial periphery of the detecting element 4. In addition, a crimping ring 112 is disposed between the ceramic sleeve 6 and a rear end portion 104 of the metal shell 102, and a metal cup 129 is disposed between the ceramic holder 106 and the shelf portion 107 of the metal shell 102. The rear end portion 104 of the metal shell 102 is crimped so as to press the ceramic sleeve 6 toward the leading end side through the crimping ring 112.

Figure 2:
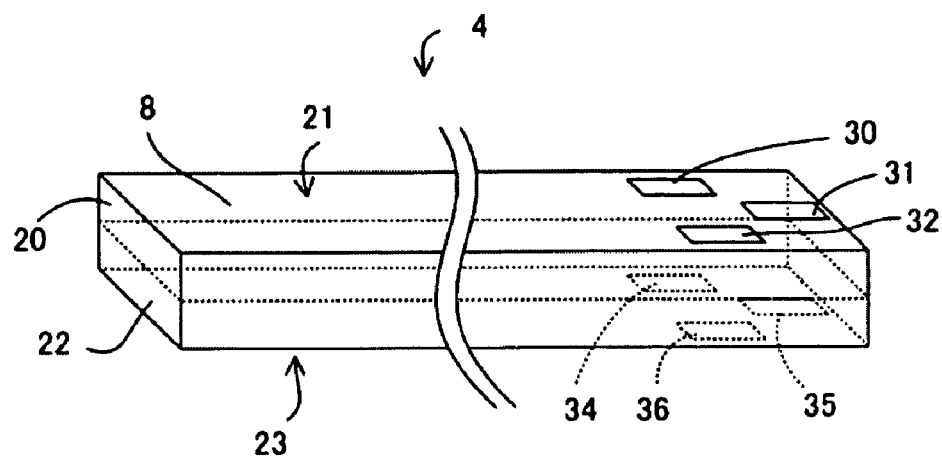
FIG. 2 is a perspective view illustrating a schematic structure of a detecting element.

Here, a perspective view illustrating a schematic structure of the detecting element 4 is shown in FIG. 2. It should be noted that the detecting element 4 is shown in FIG. 2 by omitting an axially intermediate portion.

The detecting element 4 has an element portion 20 formed in the shape of a plate extending in the axial direction (in the left-right direction in FIG. 2) as well as the heater 22 similarly formed in the shape of a plate extending in the axial direction. The element portion 20 and the heater 22 are stacked, and the detecting element 4 is formed into the shape of a plate having a rectangular axial cross section. As for the detecting element 4 which is used as the $NO_x$ sensor 2, a detailed description of its internal structure and the like will be omitted, but its rough configuration is as follows.

First, the element portion 20 is composed of an oxygen concentration detecting cell in which porous electrodes are formed on both sides of a solid electrolyte substrate; an oxygen pump cell similarly having porous electrodes formed on both sides of a solid electrolyte substrate; a $NO_x$ detecting cell similarly having porous electrodes formed on both sides of a solid electrolyte substrate; and spacers which are stacked between these cells to form a hollow measurement gas chamber. This solid electrolyte substrate is formed of zirconia in which yttria is solidly dissolved as a stabilizer. The porous electrodes are formed principally of Pt. In addition, the spacers for forming the measurement gas chamber are constituted mainly of alumina and are arranged such that one porous electrode of the oxygen concentration detecting cell, one porous electrode in the oxygen pump cell, and one porous electrode of the $NO_x$ detecting cell are exposed inside the hollow measurement gas chamber. The hollow measurement gas chamber is formed so as to be located on the leading end side of the element portion 20, and a portion where this measurement gas chamber is formed corresponds to the detecting portion 8.

The heater 22 is formed such that a heating resistor pattern is sandwiched between a pair of insulating substrates formed principally of alumina.

In addition, a protective layer (not shown) for preventing poisoning is formed on the leading end-side surface of the detecting element 4 where the detecting portion 8 is formed.

In the above-described detecting element 4, as shown in FIG. 2, the three electrode terminal portions 30, 31 and 32 are formed on the rear end side (right side in FIG. 2) of the first plate surface 21, while the three electrode terminal portions 34, 35 and 36 are formed on the rear end side of the second plate surface 23. Of these six electrode terminal portions 30, 31, 32, 34, 35 and 36, four electrode terminal portions are connected to the porous electrodes (porous electrodes of the oxygen concentration detecting cell, the oxygen pump cell, and the $NO_x$ detecting cell) provided in the element portion 20, and the remaining two are respectively connected to both ends of the heating resistor pattern provided in the heater 22.

In the detecting element 4 of this embodiment, the electrode terminal portion 31 is formed on a rearmost end region of the first plate surface 21, and the electrode terminal portions 30 and 32 are formed on the rear end portion of the first plate surface 21 in a region closer to the leading end side than the electrode terminal portion 31. In addition, in the detecting element 4 of this embodiment, the electrode terminal portion 35 is formed on a rearmost end region of the second plate surface 23, and the electrode terminal portions 34 and 36 are formed on the rear end portion of the second plate surface 23 in a region closer to the leading end side than the electrode terminal portion 35.

As shown in FIG. 1, the detecting element 4 configured as described above is fixed inside the metal shell 102 in a state in which the detecting portion 8 on the leading end side (lower side in FIG. 1) protrudes from the leading end of the metal shell 102 which is fixed to the exhaust pipe, while the electrode terminal portions 30, 31, 32, 34, 35 and 36 on the rear end side protrude from the rear end of the metal shell 102.

Meanwhile, as shown in FIG. 1, an outer protector 42 and an inner protector 43 of a double structure formed of a metal (such as stainless steel) and having a plurality of holes are attached to an outer periphery on the leading end side (lower side in FIG. 1) of the metal shell 102 by welding or the like so as to surround the protruding portion of the detecting element 4.

Further, an outer cylinder 44 is fixed to a rear end side outer periphery of the metal shell 102. In addition, a grommet 50 having therein a lead wire insertion hole 61 is formed in an opening 45 on the rear end side (upper side in FIG. 1) of the outer cylinder 44. The six lead wires 46, which are respectively electrically connected to the electrode terminal portions 30, 31, 32, 34, 35 and 36 of the detecting element 4, are inserted into the lead wire insertion hole 61.

In addition, the insulating separator 82 is disposed on the rear end side (upper side in FIG. 1) of the detecting element 4 protruding from the rear end portion 104 of the metal shell 102. The insulating separator 82 is disposed around the electrode terminal portions 30, 31, 32, 34, 35 and 36 which are formed on the rear end-side surfaces of the detecting element 4.

Next, a description will be given of the insulating separator 82.

As shown in FIG. 1, the insulating separator 82 is configured by including an outer separator 183 having the element insertion hole 84 penetrating in the axial direction, as well as a pair of inner separators 185 each having at least a portion thereof disposed in the element insertion hole 84.

Figure 3:
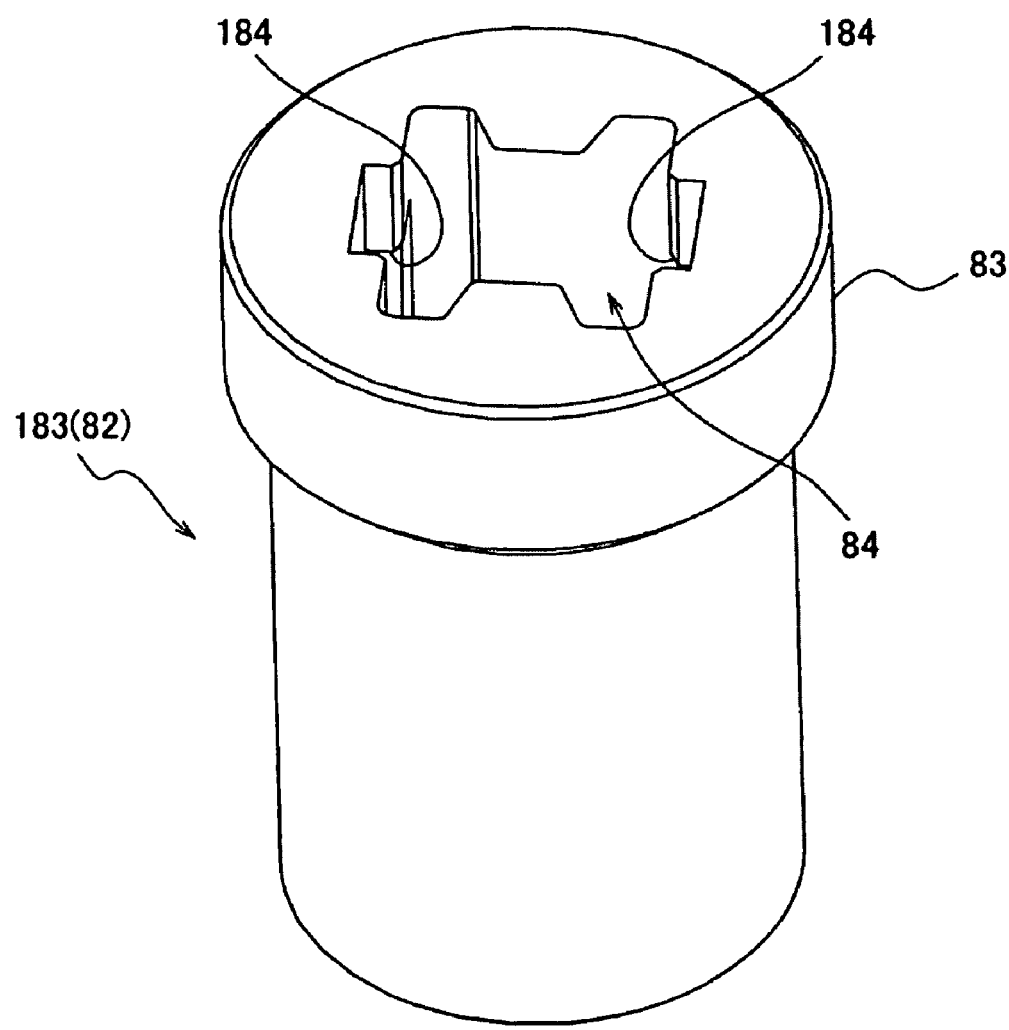
FIG. 3 is a perspective view of an outer separator when viewed in a diagonal direction from the rear end side.
Figure 4:
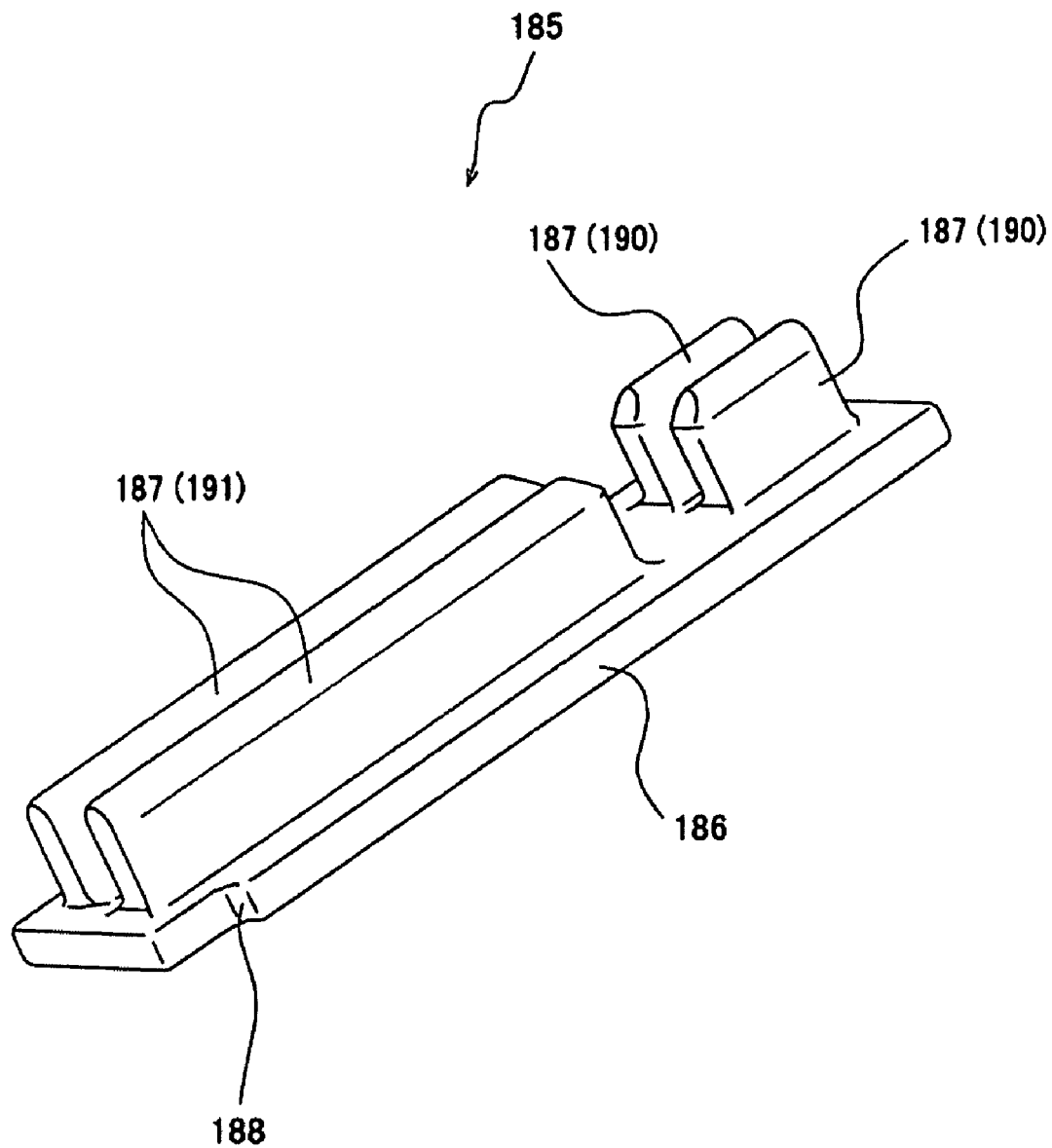
FIG. 4 is a perspective view of an inner separator.

FIG. 3 shows a perspective view, taken from a diagonal direction from the rear end side, of the outer separator 183, and FIG. 4 shows a perspective view of the inner separator 185.

As shown in FIG. 3, the outer separator 183 is formed of an insulating material (such as alumina), is formed in a cylindrical shape having the element insertion hole 84 penetrating in the axial direction, and has on its outer surface a collar portion 83 projecting radially outward.

As shown in FIG. 1, the outer separator 183 is disposed inside the outer cylinder 44 in a state in which the collar portion 83 abuts against an inner supporting member 64. The inner supporting member 64 is supportedly held inside the outer cylinder 44 by an inwardly crimped portion of the outer cylinder 44. The inner supporting member 64 thus held in the outer cylinder 44 supports the insulating separator 82 (outer separator 183) by abutting against the collar portion 83.

Figure 5:
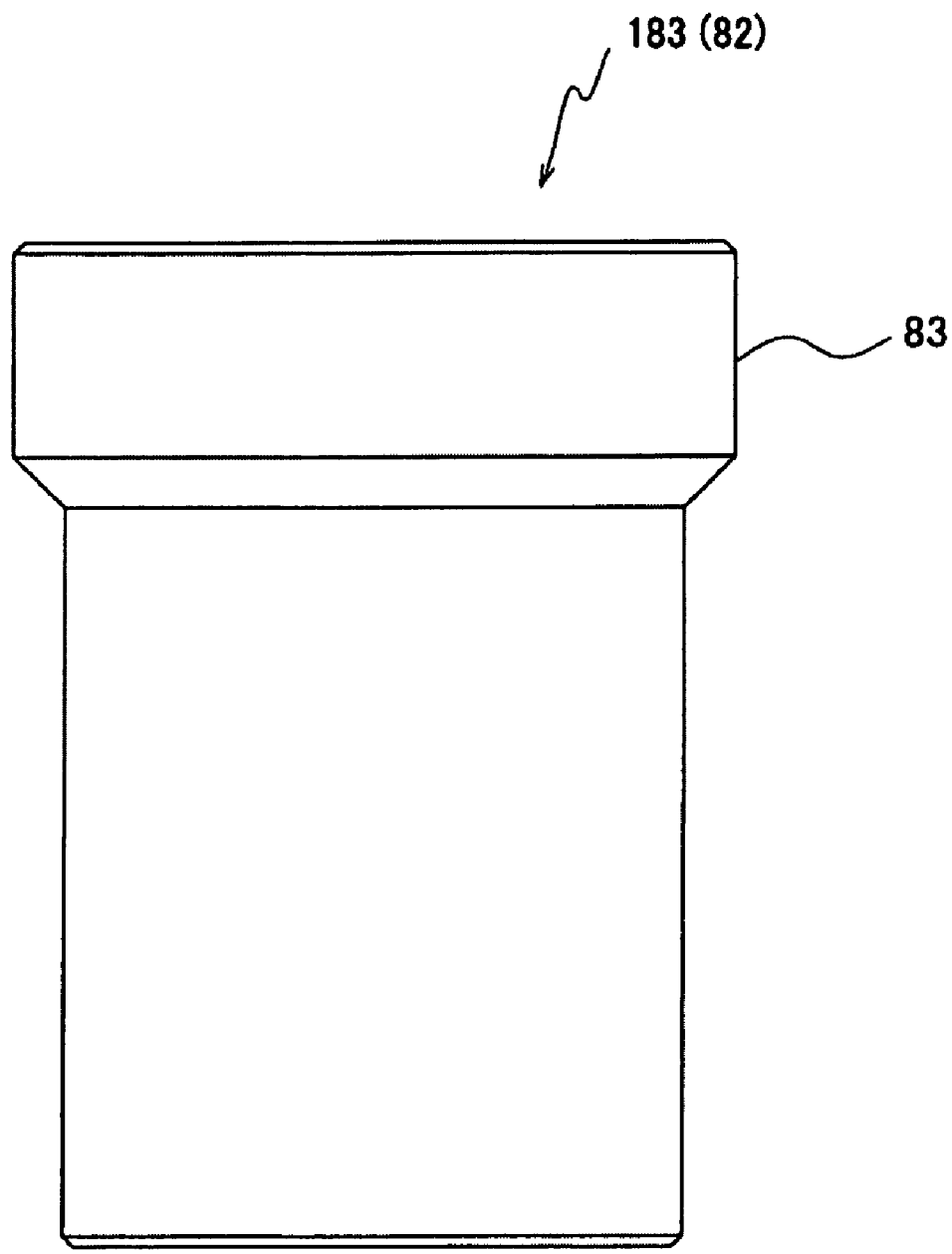
FIG. 5 is a front elevational view of the outer separator.
Figure 6:
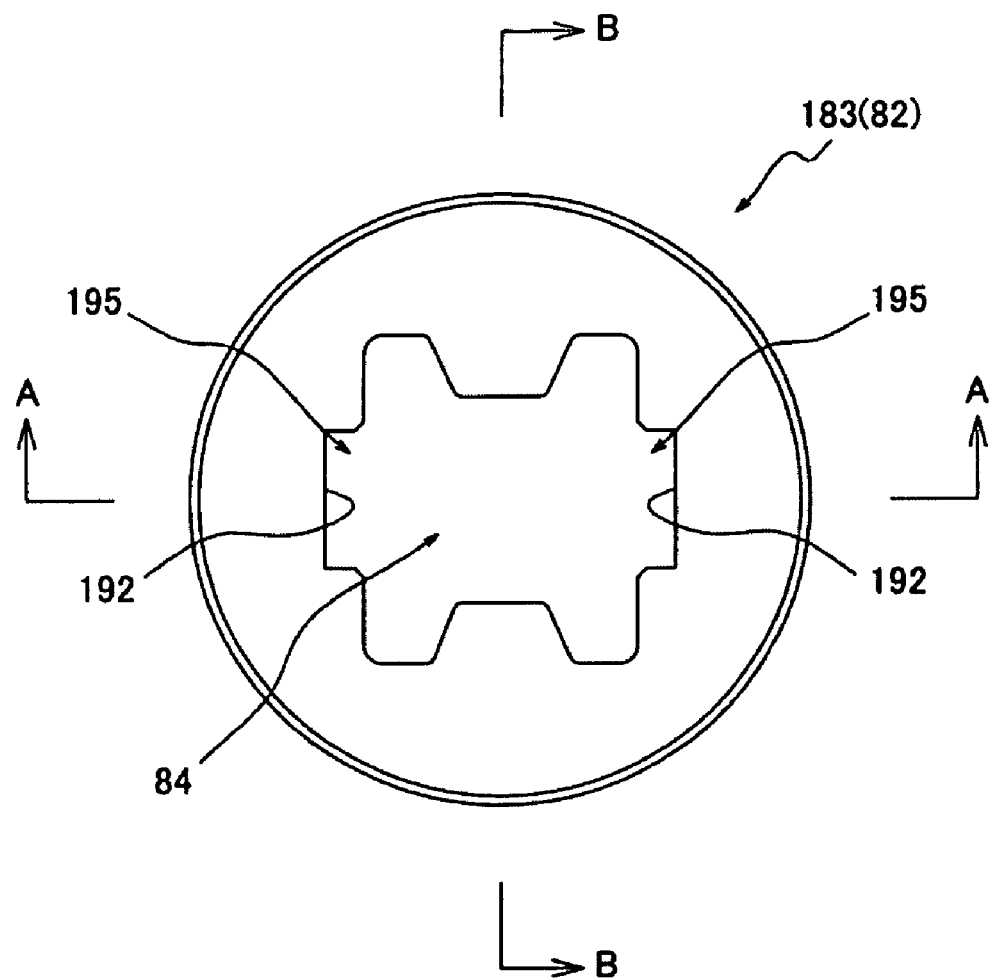
FIG. 6 is a plan view of the outer separator.
Figure 7:
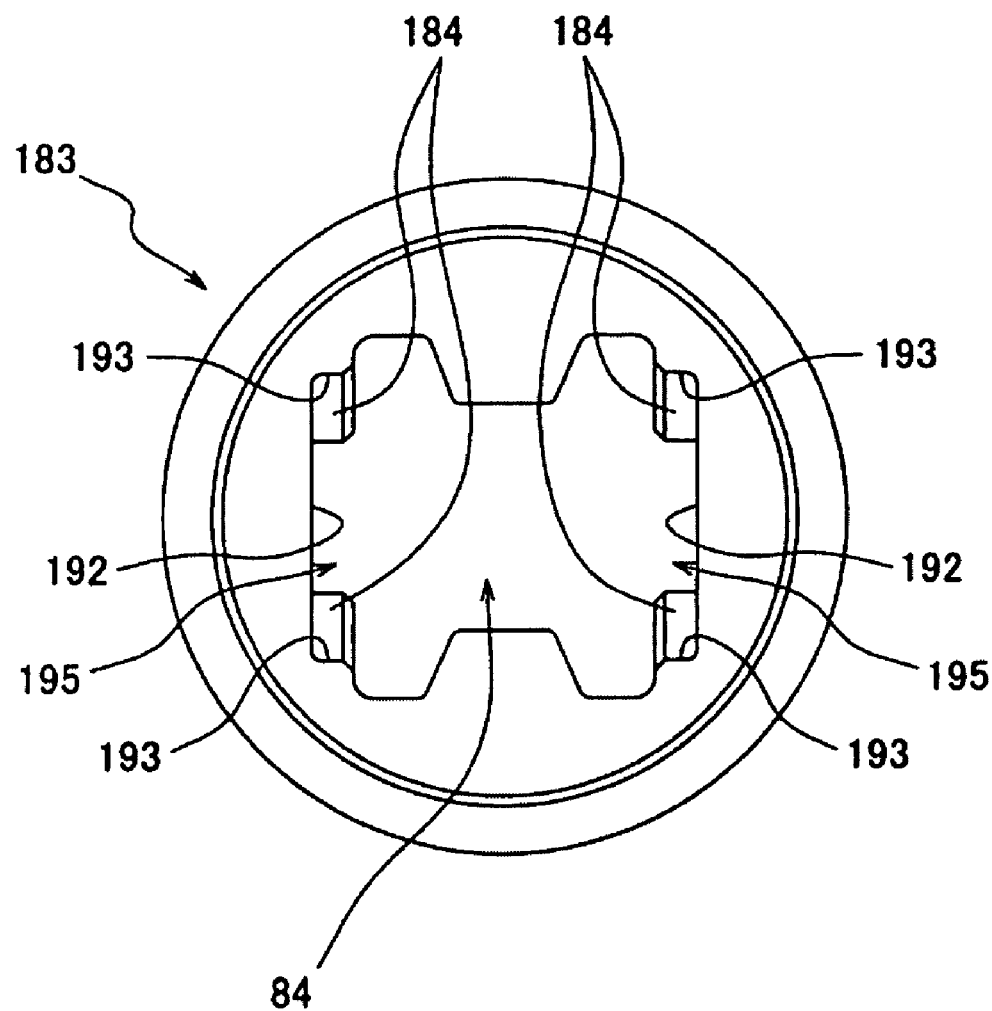
FIG. 7 is a bottom view of the outer separator.
Figure 8:
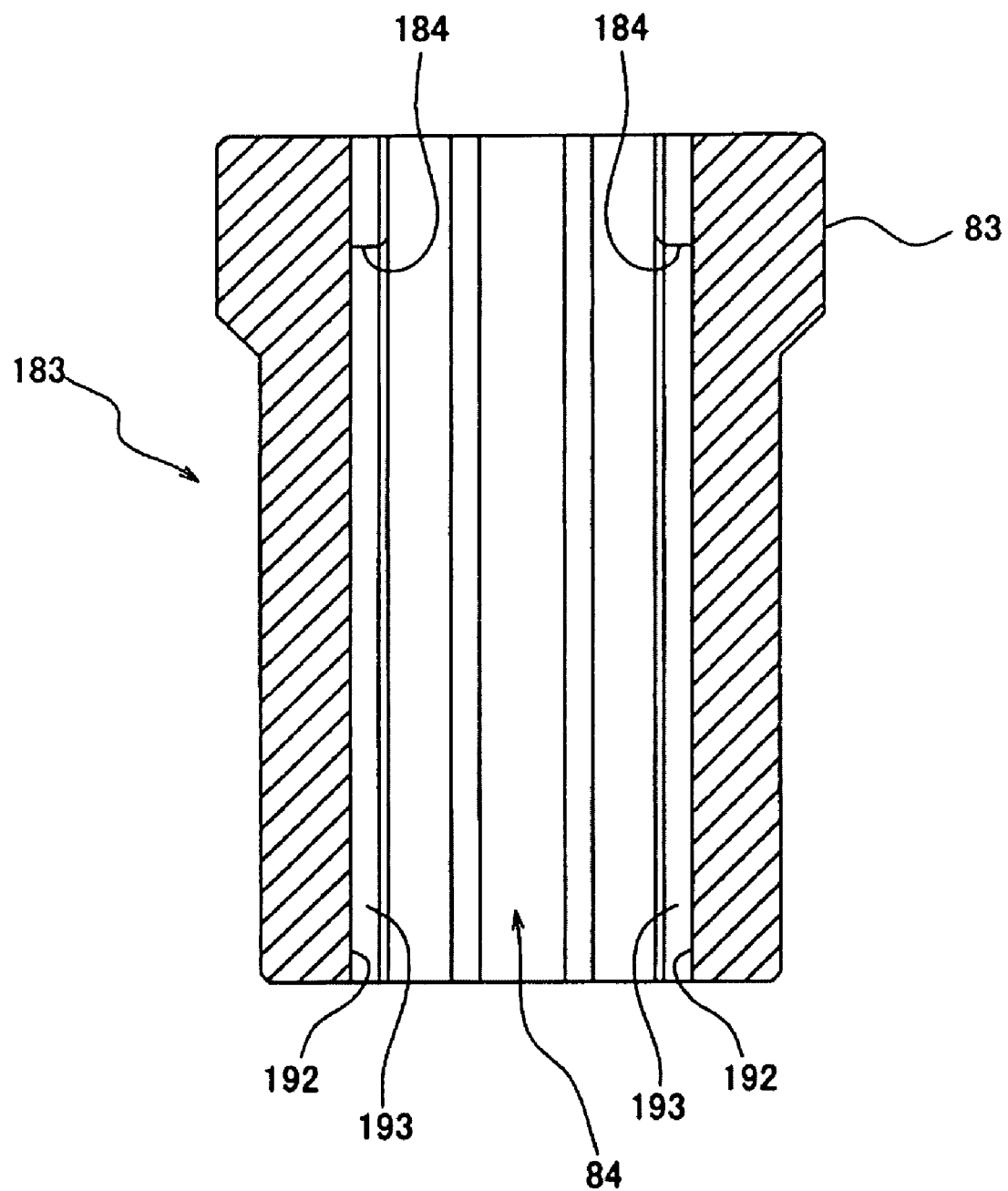
FIG. 8 is a cross-sectional view, taken along line A-A in FIG. 6, of the outer separator.
Figure 9:
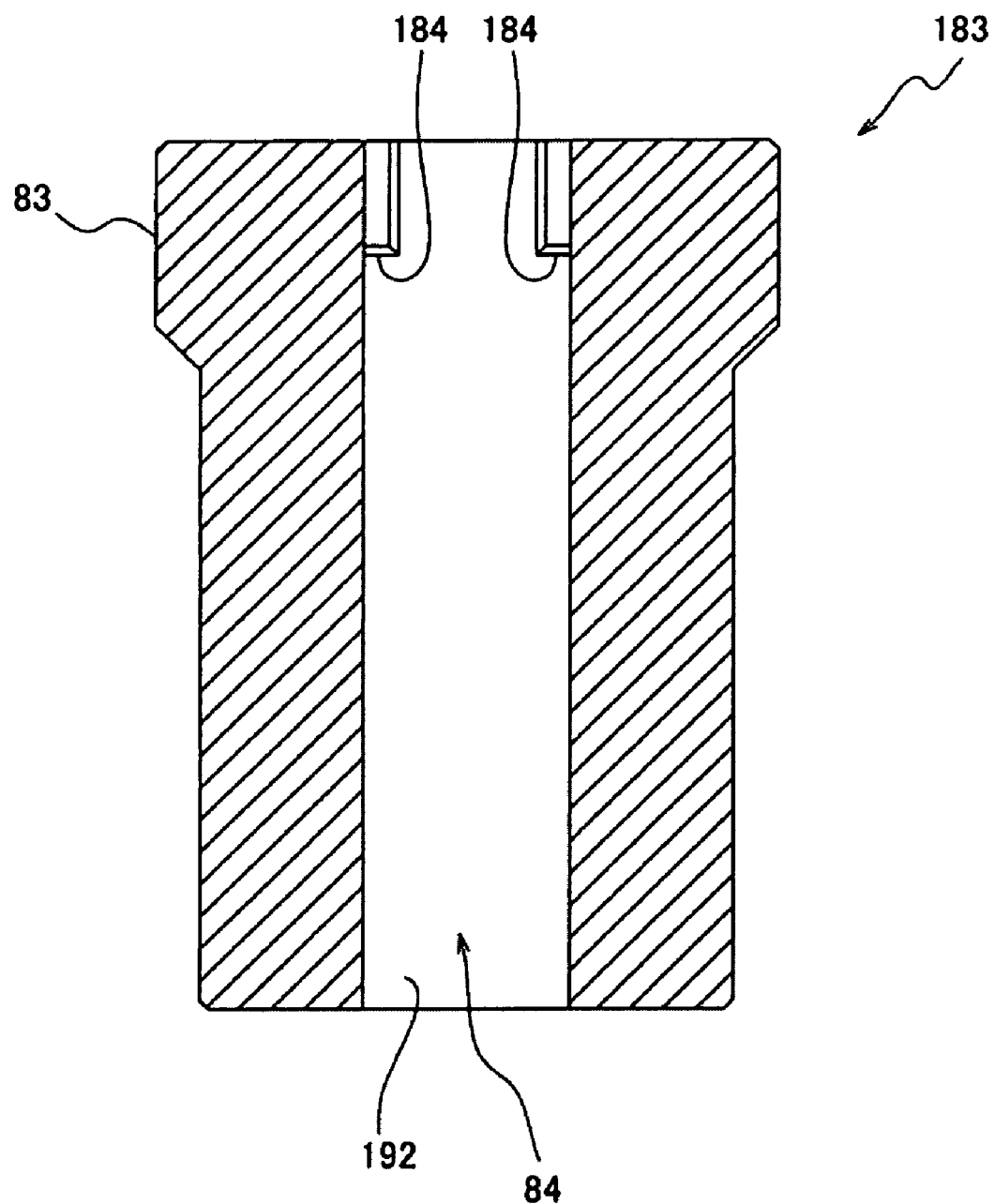
FIG. 9 is a cross-sectional view, taken along line B-B in FIG. 6, of the outer separator.

Here, to illustrate a detailed configuration of the outer separator 183, FIG. 5 shows a front elevational view of the outer separator 183, FIG. 6 shows a plan view of the outer separator 183, and FIG. 7 shows a bottom view of the outer separator 183. In addition, FIG. 8 shows a cross-sectional view, taken along line A-A in FIG. 6, of the outer separator 183, and FIG. 9 shows a cross-sectional view, taken along line B-B in FIG. 6, of the outer separator 183.

As shown in FIGS. 3, 7, 8 and 9, the outer separator 183 has on the inner surface of its element insertion hole 84 a pair of rear-surface abutting portions 192 each adapted to abut against the rear surface of each inner separator 185 and two pairs of side-surface abutting portions 193, each side-surface abutting portion 193 being adapted to abut against the respective side surface of each inner separator 185. Further, a recessed portion 195, which is surrounded by the rear-surface abutting portion 192 and the pair of side-surface abutting portions 193 in the element insertion hole 84, serves as a region where the inner separator 185 is disposed.

In addition, as shown in FIGS. 3, 7, 8 and 9, the outer separator 183 has two pairs of position determining portions 184 projecting inward on the rear end side in the element insertion hole 84. Each of these position determining portions 184 has an engaging face opposing the leading end side in the axial direction, and as this engaging face engages a rear end face (rear opposing face) of the inner separator 185, the inner separator 185 is positioned inside the element insertion hole 84.

Next, a description will be given of the inner separator 185.

As shown in FIG. 4, the inner separator 185, which is formed of an insulating material, includes a plate-shaped body portion 186 and partition walls 187 projecting from the plate surface of the plate-shaped body portion 186.

Figure 10:
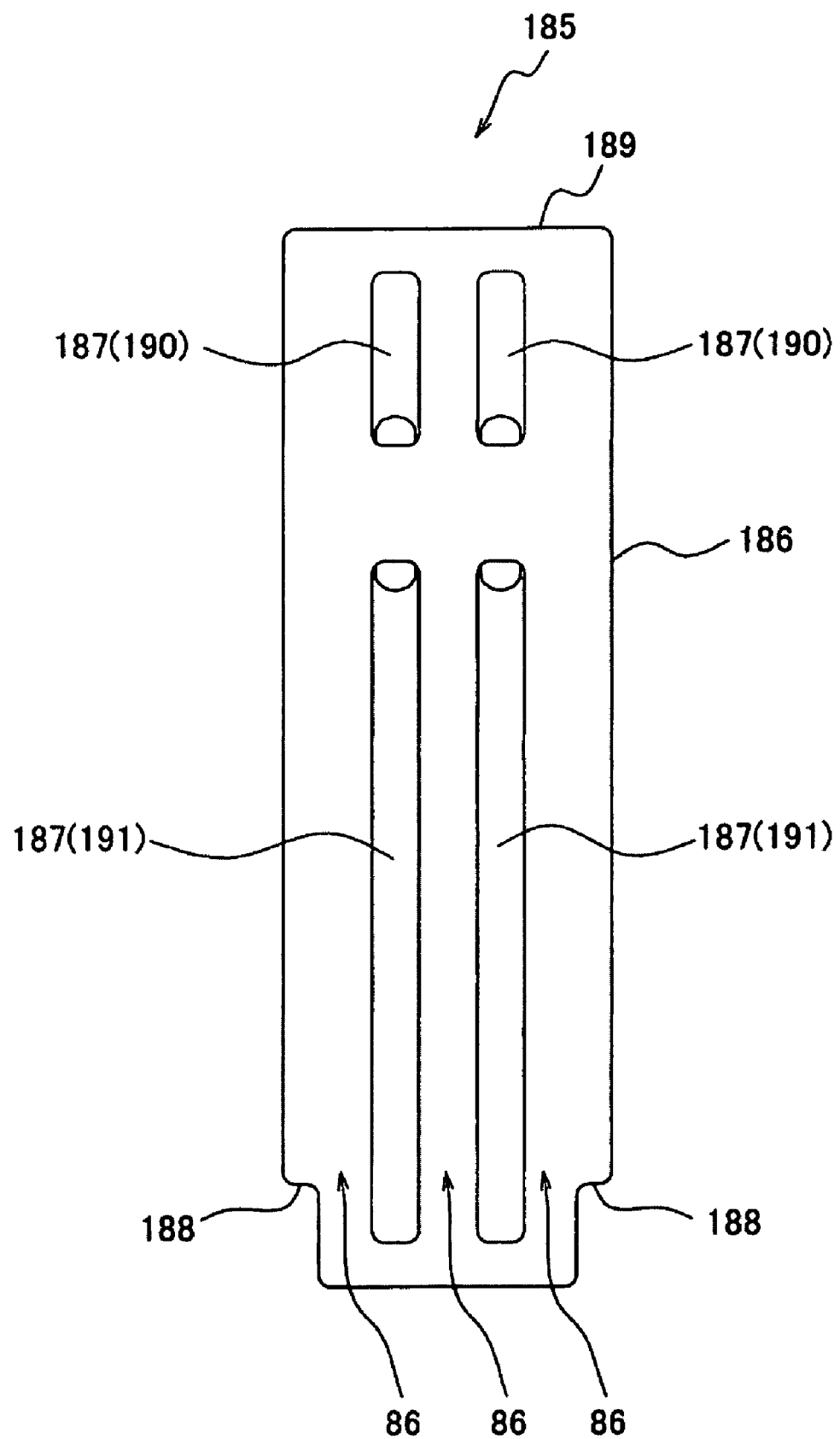
FIG. 10 is a front elevational view of the inner separator.
Figure 11:
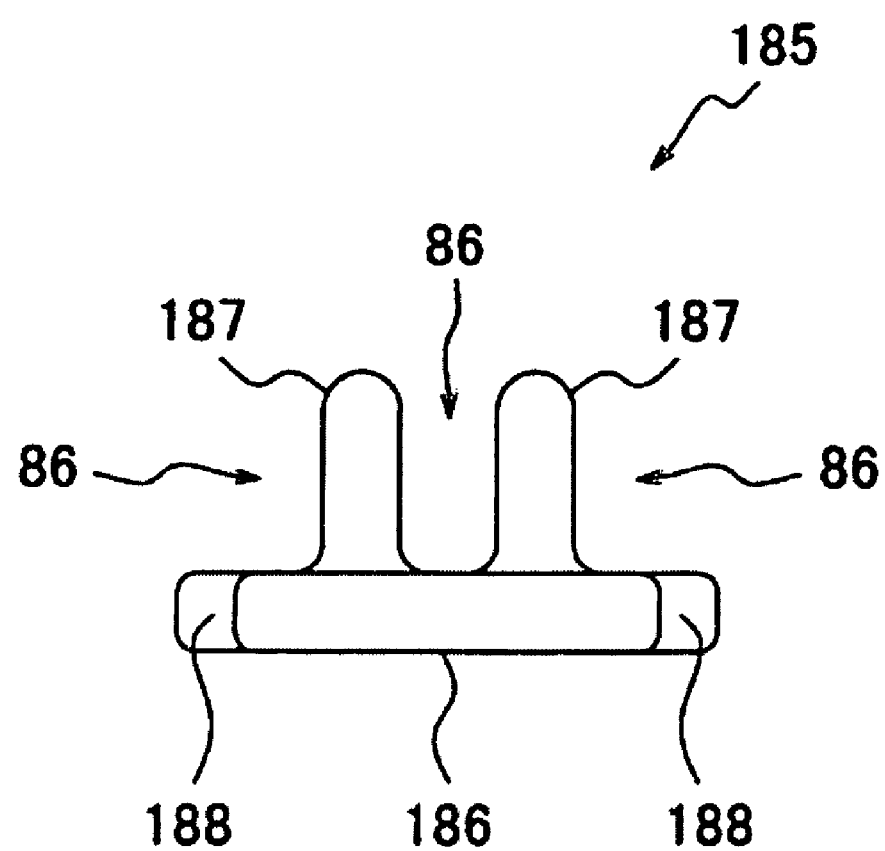
FIG. 11 is a bottom view of the inner separator.

Here, FIG. 10 shows a front elevational view of the inner separator 185, and FIG. 11 shows a bottom view (an external view taken from the leading end side) of the inner separator 185. In FIG. 10, the upper side in the drawing is the rear end side, and the lower side in the drawing is the leading end side.

The plate-shaped body portion 186 has its widthwise dimension (left-right dimension in FIG. 10) set to a size that allows the plate-shaped body portion 186 to be inserted in the recessed portion 195 of the element insertion hole 84 of the outer separator 183.

Further, the arrangement position of the plate-shaped body portion 186 in the element insertion hole 84 is determined such that its rear surface is opposed to the rear-surface abutting portion 192 of the outer separator 183, its both side surfaces are respectively opposed to the side-surface abutting portions 193 of the outer separator 183, and its rear end portion 189 is engaged with the pair of position determining portions 184 (see FIGS. 7, 8 and 9) of the outer separator 183.

In addition, the plate-shaped body portion 186 has a pair of notched portions 188 which are formed by cutting two corners off of its leading end side (lower end in FIG. 10). This notched portion 188 is formed to allow a portion (a below-described terminal retaining portion 318) of the leadframe 10 to abut against the notched portion 188. Further, the portion (the below-described terminal retaining portion 318) of the leadframe 10 abuts against the notched portion 188, so as to prevent the inner separator 185 from coming off the element insertion hole 84 of the outer separator 183.

Next, as for the partition walls 187, four pieces are provided on the plate surface of the plate-shaped body portion 186, and are formed in two rows so as to extend in the axial direction (in the vertical direction in FIG. 10). Of the partition walls 187, two pieces which are formed on the rear end side (upper side in FIG. 10) are rear end partition walls 190, while two pieces which are formed on the leading end side (lower side in FIG. 10) are leading end partition walls 191.

Further, the partition walls 187 are formed in two rows, and the plate surface of the plate-shaped body portion 186 is divided into three parts to form three frame arranging grooves 86 (i.e., regions where the leadframes 10 are arranged). Namely, the partition walls 187 are provided as boundary portions of the frame arranging grooves 86 (regions where the leadframes 10 are arranged).

The partition walls 187 prevent the leadframes 10 from coming into contact with one another by suppressing movement of the leadframes 10 in the widthwise direction (left-right direction in FIG. 10) of the plate-shaped body portion 186. As a result, the frame arranging grooves 86 serve as arranging regions for individually arranging the three leadframes 10 in a mutually electrically insulated state.

In addition, the partition wall 187 is divided into a rear end partition wall 190 and a leading end partition wall 191. A portion (a below-described frame retaining portion 219) of the leadframe 10 is disposed in a gap region between the rear end partition wall 190 and the leading end partition wall 191, so as to suppress movement of the leadframe 10 in the axial direction.

Since the inner separator 185 has the partition walls 187, the structure becomes such that the positioning (positioning in the axial direction) of the leadframe 10 in the element insertion hole 84 of the outer separator 183 is facilitated.

Next, a description will be given of the leadframes 10.

The leadframes 10 are formed of a known material which is capable of maintaining elasticity (spring elasticity) even if repeatedly exposed to high temperature (e.g., INCONEL, stainless steel, or the like).

The $NO_x$ sensor 2 in this embodiment includes three kinds of leadframes (first leadframe 211, second leadframe 221, and third leadframe 231) each having different shapes. In addition, in FIG. 1, to facilitate an understanding of the internal structures of the insulating separator 82 and the grommet 50, the cross-sectional state of the arrangement region of the first leadframe 211 is shown in the right half portion, while the cross-sectional state of the arrangement region of the third leadframe 231 is shown in the left half portion.

First, a description will be given of the first leadframe 211.

Figure 12:
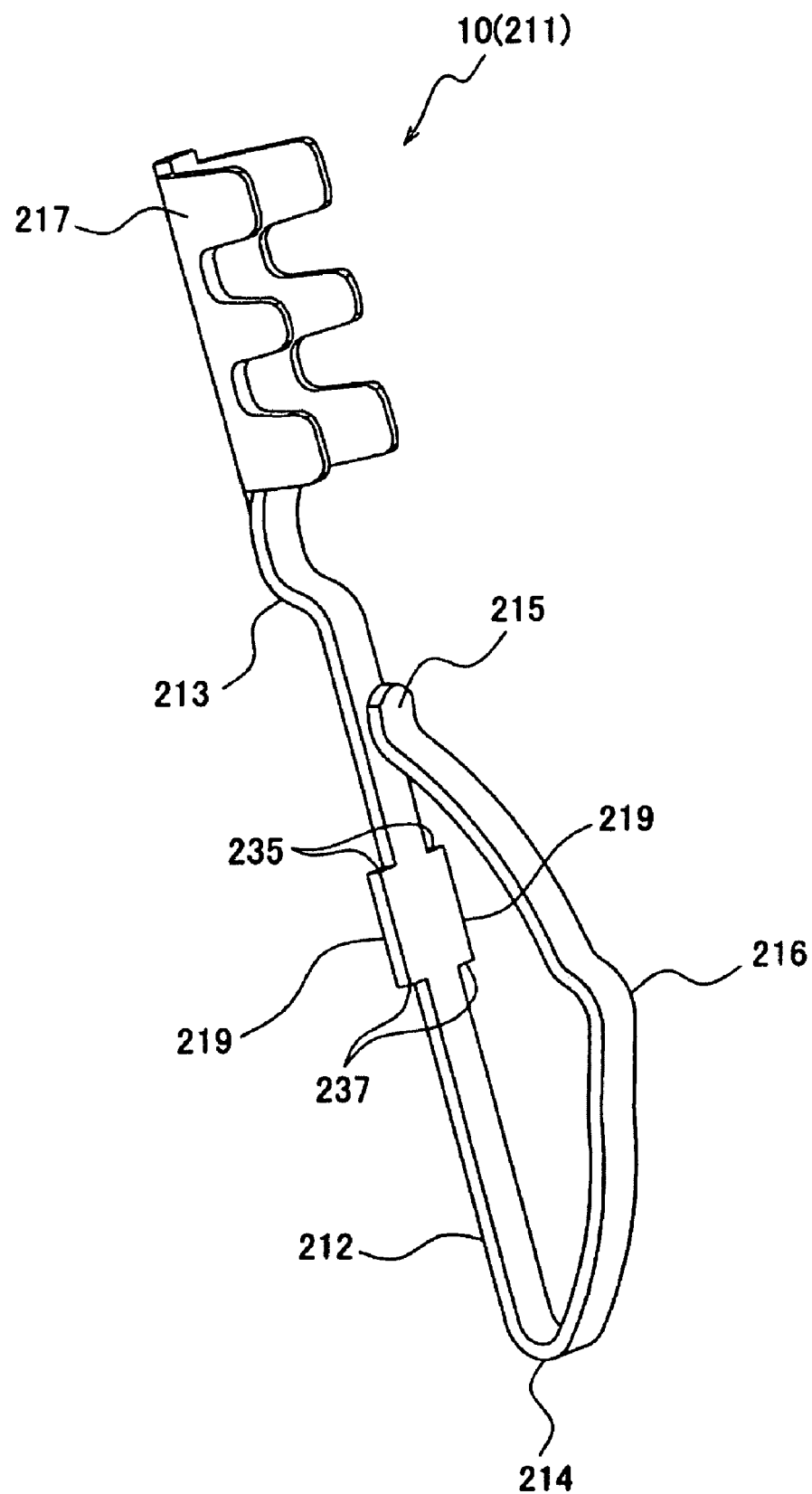
FIG. 12 is a perspective view of a first leadframe.

A perspective view of the first leadframe 211 is shown in FIG. 12.

The first leadframe 211 has a frame body portion 212 formed of an elongated plate-like member extending in the axial direction as well as an element abutting portion 216 which extends from a leading end of the frame body portion 212 such that at least a portion thereof is disposed between the frame body portion 212 and the detecting element 4. In addition, the first leadframe 211 is so arranged that the element abutting portion 216 (specifically, a portion of the element abutting portion 216) abuts against an electrode terminal portion of the detecting element 4.

A connecting portion 214, which is connected to the leading end of the frame body portion 212 and makes a change in direction toward the radially inward side, is adapted to undergo elastic deformation upon application of an external force thereto. Namely, as for the first leadframe 211, a gap interval between the frame body portion 212 and the element abutting portion 216 is adapted to change as the connecting portion 214 undergoes elastic deformation.

The frame body portion 212 has a curved portion 213 which is curved in the thicknesswise direction of the plate surface. The arrangement is such that, with regard to the leading end-side portion of the frame body portion 212 (located closer to the leading end side than the curved portion 213) and the rear end-side portion of the frame body portion 212 (located closer to the rear end side than the curved portion 213), their respective positions in the thicknesswise direction of the plate surface are made mutually different.

Further, the first leadframe 211 has a pair of frame retaining portions 219 formed so as to project in the widthwise direction from both side surfaces of the frame body portion 212.

The frame retaining portion 219 is sized so that it can be disposed between the rear end partition wall 190 and the leading end partition wall 191 in the inner separator 185 of the insulating separator 82. The frame retaining portion 219 has a first retaining surface 235 opposing the axial rear end side of the frame body portion 212 and a second retaining surface 237 opposing the axial leading end side of the frame body portion 212.

Namely, if the frame retaining portion 219 of the first leadframe 211 is disposed between the rear end partition wall 190 and the leading end partition wall 191, the first retaining surface 235 abuts against the rear end partition wall 190, while the second retaining surface 237 abuts against the leading end partition wall 191. Thus, by disposing the frame retaining portion 219 between the rear end partition wall 190 and the leading end partition wall 191, it is possible to prevent a change in the relative position (relative axial position) of the first leadframe 211 with respect to the insulating separator 82 (inner separator 185).

The element abutting portion 216 is connected to the leading end of the frame body portion 212 and is formed such that, in a free state of the first leadframe 211, a fee-side end portion 215, i.e., an axial rear end portion, of the element abutting portion 216 is spaced apart from the frame body portion 212. In addition, the element abutting portion 216 is formed with a curved circular arc shape such that an interval dimension from its axially intermediate portion to the frame body portion 212 is longer than an interval dimension from its free-side end portion 215 to the frame body portion 212, and such that a protruding-side surface of the circular arc shape abuts against the detecting element 4.

The element abutting portion 216 is arranged such that its free-side end portion 215 abuts against the frame body portion 212 as its connecting portion 214 is elastically deformed to cause the free-side end portion 215 to approach the frame body portion 212. In addition, the element abutting portion 216 is curved such that its substantially axially intermediate portion projects toward the detecting element 4.

In other words, the first leadframe 211 is sandwiched between the detecting element 4 and the insulating separator 82 (inner separator 185) and is arranged such that when the connecting portion 214 is elastically deformed, the free-side end portion 215 of the element abutting portion 216 abuts against the frame body portion 212, while the element abutting portion 216 abuts against the electrode terminal portion of the detecting element 4.

Further, the first leadframe 211 has at a rear end portion (upper end portion in FIG. 12) of the frame body portion 212 a lead wire connecting portion 217 having a greater width than the frame body portion 212. This lead wire connecting portion 217, after being formed into a substantially cylindrical shape by bending, is electrically connected to the lead wire 46 by crimping radially inwardly with a core wire of the lead wire 46 (see FIG. 1) inserted therein.

Next, a description will be given of the second leadframe 221.

Figure 13:
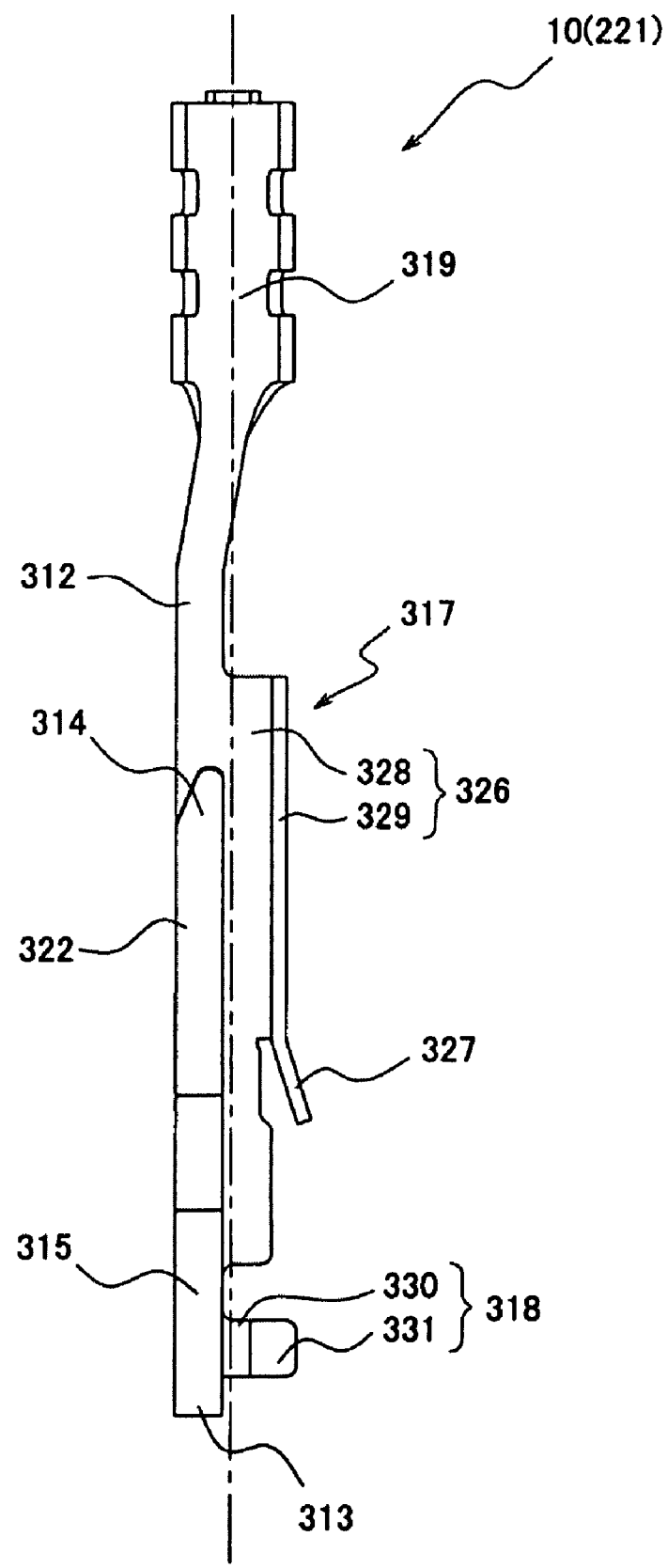
FIG. 13 is a front elevational view of a second leadframe.
Figure 14:
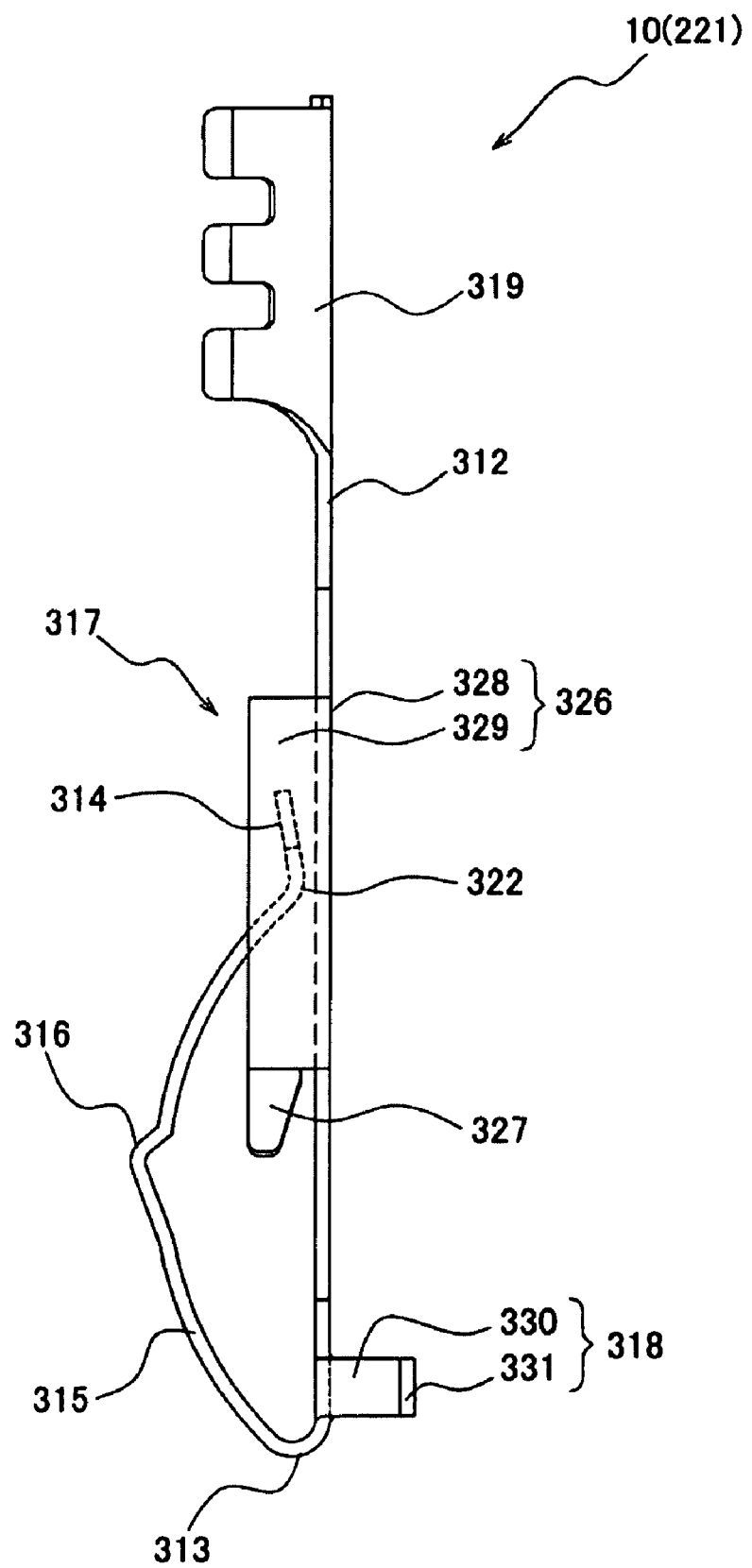
FIG. 14 is a right side view of the second leadframe.

A front elevational view of the second leadframe 221 is shown in FIG. 13, and a right side view of the second leadframe 221 is shown in FIG. 14.

The second leadframe 221 has a frame body portion 312 formed of an elongated plate-like member extending in the axial direction as well as an element abutting portion 315 which extends axially from a leading end of the frame body portion 312 such that a portion thereof is disposed between the frame body portion 312 and the detecting element 4.

The element abutting portion 315 has formed in its substantially axially intermediate portion an abutting bent portion 316 which is bent so as to project toward the detecting element 4.

In addition, the element abutting portion 315 has a connecting side end portion 313 whose leading end side is connected to the frame body portion 312 and is bent and makes a change in direction. Further, the element abutting portion 315 has on its rear end side a body abutting portion 322 which abuts against the frame body portion 312, and is formed such that, in a free state of the second leadframe 221, a free-side end portion 314, i.e., an axial rear end portion, of the element abutting portion 315 is spaced apart from the frame body portion 312.

This body abutting portion 322 abuts against the frame body portion 312 when the connecting side end portion 313 is elastically deformed as the second leadframe 221 is sandwiched between the detecting element 4 and the insulating separator 82 (inner separator 185).

In addition, the element abutting portion 315 is formed with a curved circular arc shape such that the abutting bent portion 316 on the protruding-side surface of the circular arc shape abuts against the detecting element 4. Further, when the second leadframe 221 is viewed from the detecting element 4 side, the free-side end portion 314 of the element abutting portion 315 is formed such that its portion located closer to the rear end side than the body abutting portion 322 is formed in a tapered shape.

In addition, the second leadframe 221 has at a rear end portion (upper side in FIGS. 13 and 14) of the frame body portion 312 a lead wire connecting portion 319 having a greater width than the frame body portion 312. This lead wire connecting portion 319, after being formed into a substantially cylindrical shape by bending, is connected to the lead wire 46 by crimping radially inwardly with a core wire of the lead wire 46 (see FIG. 1) inserted therein.

Further, as shown in FIGS. 13 and 14, the second leadframe 221 of this embodiment has a terminal fixing guide portion 317 which extends laterally from a substantially axially intermediate portion of the frame body portion 312. This terminal fixing guide portion 317 is formed such that its rear end portion is located closer to the axially rear end side than the rear end portion of the free-side end portion 314.

This terminal fixing guide portion 317 has a jutting-out portion 326 and a fixed contact portion 327.

The jutting-out portion 326 is configured by including a flat surface portion 328 formed flush with the frame body portion 312 and a vertical surface portion 329 extending vertically from this flat surface portion 328. Further, the jutting-out portion 326 is so arranged that the vertical surface portion 329 is disposed in the space where the element abutting portion 315 is present between the two spaces partitioned flush with the frame body portion 312.

Next, the fixed contact portion 327 extends from the axial leading end side in the vertical surface portion 329 of the jutting-out portion 326.

The fixed contact portion 327 is bent at a predetermined angle (e.g., about 30°) with respect to the plate surface of the vertical surface portion 329 so as to move away from the frame body portion 312, and is formed with a tapered shape in which its width becomes gradually narrow toward the leading end side. In addition, a leading end portion of this fixed contact portion 327 extending in the tapered shape is formed in a circular arc shape. Further, this fixed contact portion 327 is formed so as to be elastically deformed toward the frame body portion 312 side when an external force directed toward the frame body portion 312 is applied to its leading end side.

In addition, the second leadframe 221 has a terminal retaining portion 318 extending from the leading end side of the frame body portion 312.

The terminal retaining portion 318 includes an extended portion 330 extending from a side surface on the leading end side of the frame body portion 312 as well as a vertical portion 331 extending from an end of the extended portion. The extended portion 330 is configured to have a plate surface perpendicular to the plate surface of the frame body portion 312, and the vertical portion 331 is configured to have a plate surface parallel to the plate surface of the frame body portion 312.

Further, when the second leadframe 221 is disposed in the element insertion hole 84 of the insulating separator 82, the arrangement position of the second leadframe 221 in the element insertion hole 84 is determined as the terminal retaining portion 318 abuts against the notched portion 188 of the insulating separator 82 (specifically, the plate-shaped body portion 186). Namely, as the terminal retaining portion 318 of the leadframe 10 abuts against the notched portion 188 of the insulating separator 82 (specifically, the inner separator 185), it is possible to set the relative position between the insulating separator 82 and the leadframe 10.

Next, a description will be given of the third leadframe 231.

The third leadframe 231 is configured by modifying the second leadframe 221 bilaterally axisymmetrically, and is configured to have a terminal fixing guide portion corresponding to the terminal fixing guide portion 317 of the second leadframe 221 and a terminal retaining portion corresponding to the terminal retaining portion 318 of the second leadframe 221.

Namely, the third leadframe 231 is configured such that the second leadframe 221 shown in FIG. 13 becomes axisymmetric about a center axis (chain line in FIG. 13). For this reason, a detailed illustration of the third leadframe 231 will be omitted.

When the leadframes 10 thus configured are arranged on the inner separator 185, the first leadframe 211 is arranged in a centrally positioned one of the three frame arranging grooves 86 shown in FIG. 10, the second leadframe 221 is arranged in a right-end one of the three frame arranging grooves 86, and the third leadframe 231 is arranged in a left-end one of the three frame arranging grooves 86.

In other words, the first leadframe 211 is arranged in the frame arranging groove 86 corresponding to the electrode terminal portions 31 and 35 of the detecting element 4, the second leadframe 221 is arranged in the frame arranging groove 86 corresponding to the electrode terminal portions 30 and 36 of the detecting element 4, and the third leadframe 231 is arranged in the frame arranging groove 86 corresponding to the electrode terminal portions 32 and 34 of the detecting element 4.

Next, a description will be given of the operational procedure for arranging the leadframes 10 in the element insertion hole 84 of the insulating separator 82.

Figure 15:
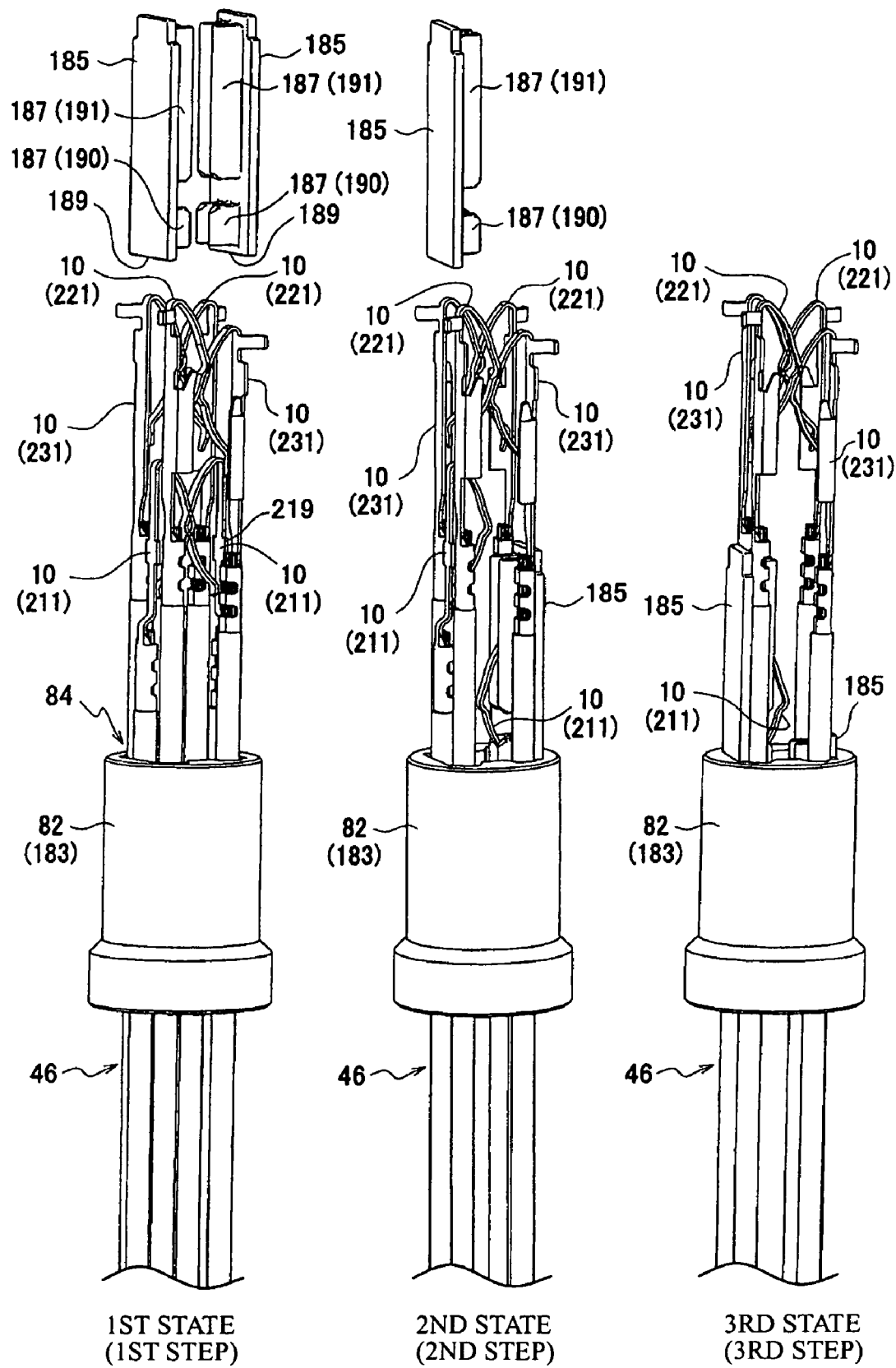
FIG. 15 is an explanatory diagram illustrating a first state to a third state in the course of arranging the leadframes in an element insertion hole of an insulating separator.
Figure 16:
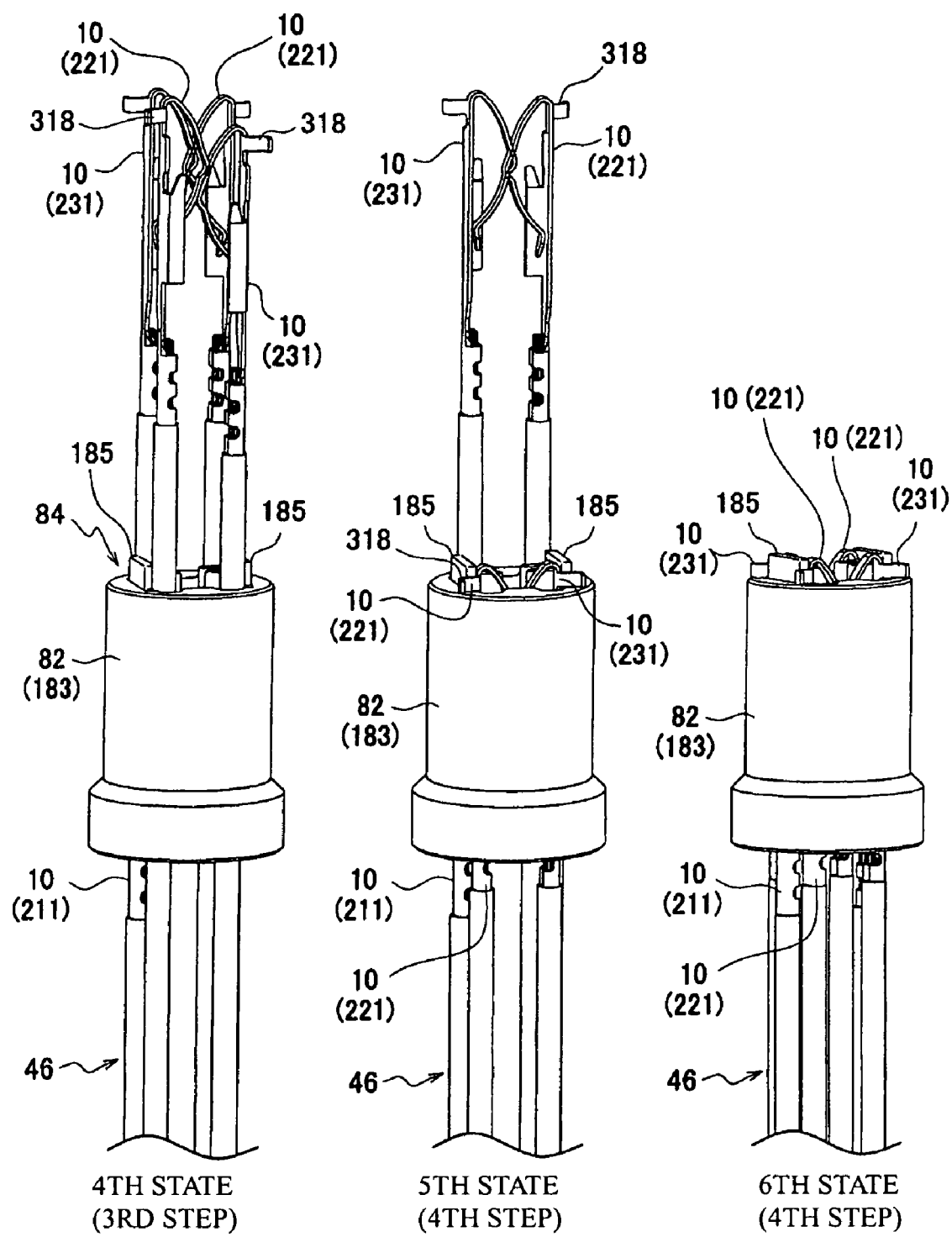
FIG. 16 is an explanatory diagram illustrating a fourth state to a sixth state in the course of arranging the leadframes in the element insertion hole of the insulating separator.

FIGS. 15 and 16 are explanatory diagrams illustrating successive states in arranging the leadframes 10 with respect to the element insertion hole 84 of the insulating separator 82. In FIGS. 15 and 16, the respective component members are illustrated such that the upper side of the drawing is set as the leading end side of the $NO_x$ sensor 2, and the lower side in the drawing is set as the rear end side of the $NO_x$ sensor 2.

In a first step, in a state in which the lead wires 46 are inserted in the element insertion hole 84 of the outer separator 183, the operation of crimping and connecting the respective lead wires 46 to the lead wire connecting portions (specifically, the lead wire connecting portion 217 and the lead wire connecting portion 319) of the leadframes 10 (the first leadframe 211, the second leadframe 221, and the third leadframe 231) is performed.

At this time, the arrangement positions of the lead wires 46 in the element insertion hole 84 of the outer separator 183 are determined such that the first leadframe 211 corresponds to the electrode terminal portions 31 and 35 of the detecting element 4, the second leadframe 221 corresponds to the electrode terminal portions 30 and 36 of the detecting element 4, and the third leadframe 231 corresponds to the electrode terminal portions 32 and 34 of the detecting element 4.

The first state (the state at the left end) in FIG. 15 illustrates the state when the first step has been completed. In the explanatory diagram of the first state in FIG. 15, the two inner separators 185 which are not used in the operation of the first step are also shown for reference.

In an ensuing second step, the operation of inserting one of the two first leadframes 211 into the element insertion hole 84 of the outer separator 183 is performed by using one of the two inner separators 185.

Namely, in the state in which the first leadframe 211 is arranged in the centrally positioned frame arranging groove 86 among the three frame arranging grooves 86 (see FIG. 10) of the inner separator 185, the first leadframe 211 together with the inner separator 185 is inserted into the element insertion hole 84 of the outer separator 183.

At this time, as the frame retaining portion 219 of the first leadframe 211 is disposed between the rear-end partition wall 190 and the leading end partition wall 191, the inner separator 185 and the first leadframe 211 can be inserted into the element insertion hole 84 while maintaining a fixed relative position between the first leadframe 211 and the inner separator 185 in the axial direction.

Then, the inner separator 185 and the first leadframe 211 are inserted into the element insertion hole 84 until the rear end portion 189 of the inner separator 185 abuts against the position determining portion 184 (see FIGS. 7, 8 and 9) of the outer separator 183. As the rear end portion 189 of the inner separator 185 abuts against the position determining portion 184 of the outer separator 183, the arrangement positions of the inner separator 185 and the first leadframe 211 in the element insertion hole 84 of the outer separator 183 can be set to predetermined positions.

In addition, since the first leadframe 211 is arranged in the centrally positioned frame arranging groove 86 in the inner separator 185 and is sandwiched by the two partition walls 187, movement of the first leadframe 211 in the widthwise direction of the inner separator 185 is limited. Consequently, it is possible to prevent the first leadframe 211 from coming into contact with the other leadframes 10 (the second leadframe 221 and the third leadframe 231) adjacent to which the first leadframe 211 is arranged, to thereby prevent short circuiting.

The second state in FIG. 15 illustrates an interim stage (specifically, the stage in which a portion of the inner separator 185 has been inserted into the element insertion hole 84 of the outer separator 183) of the second step.

In an ensuing third step, the operation of inserting the other one of the two first leadframes 211 into the element insertion hole 84 of the outer separator 183 is performed by using the other one of the two inner separators 185.

Since the inserting operation is similar to the above-described details, a detailed description thereof will be omitted.

The third state in FIG. 15 illustrates an interim stage (specifically, the stage in which a portion of the inner separator 185 has been inserted into the element insertion hole 84 of the outer separator 183) of the third step. In addition, the fourth state in FIG. 16 illustrates the state when the third step has been completed.

In the ensuing fourth step, the operation of inserting the remaining four leadframes 10 (two second leadframes 221 and two third leadframes 231) into the element insertion hole 84 of the outer separator 183 is performed.

Namely, an operation is performed in which the lead wire 46 is moved toward the rear end side while the position of the insulating separator 82 is fixed by holding that portion of the lead wire 46 which is closer to the rear end side (lower side in FIG. 16) than the insulating separator 82, to thereby pull the leadframe 10 (each of the second leadframe 221 and the third leadframe 231) into the element insertion hole 84 of the outer separator 183.

At this time, the lead wire 46 is moved until the terminal retaining portion 318 of the leadframe 10 (each of the second leadframe 221 and the third leadframe 231) abuts against the notched portion 188 of the inner separator 185.

Consequently, the arrangement positions (specifically, axial arrangement positions) of the four leadframes 10 (two second leadframes 221 and two third leadframes 231) in the element insertion hole 84 of the insulating separator 82 (outer separator 183) can be set to fixed positions.

At this time, the leadframes 10 may be inserted sequentially one by one into the element insertion hole 84 of the outer separator 183, or a plurality of (e.g., two) leadframes 10 may be simultaneously inserted into the element insertion hole 84.

The fifth state in FIG. 16 illustrates the state of an interim stage (specifically, the stage in which two of the four leadframes 10 have been inserted into the element insertion hole 84 of the outer separator 183) of the fourth step. In addition, the sixth state in FIG. 16 illustrates the state when the fourth step has been completed.

As the inner separators 185 and the leadframes 10 are thus arranged in the element insertion hole 84 of the outer separator 183, the insulating separator 82 having the inner separators 185 and the outer separator 183 is completed, and the six leadframes 10 are arranged in the element insertion hole 84 of the insulating separator 82.

Figure 17:
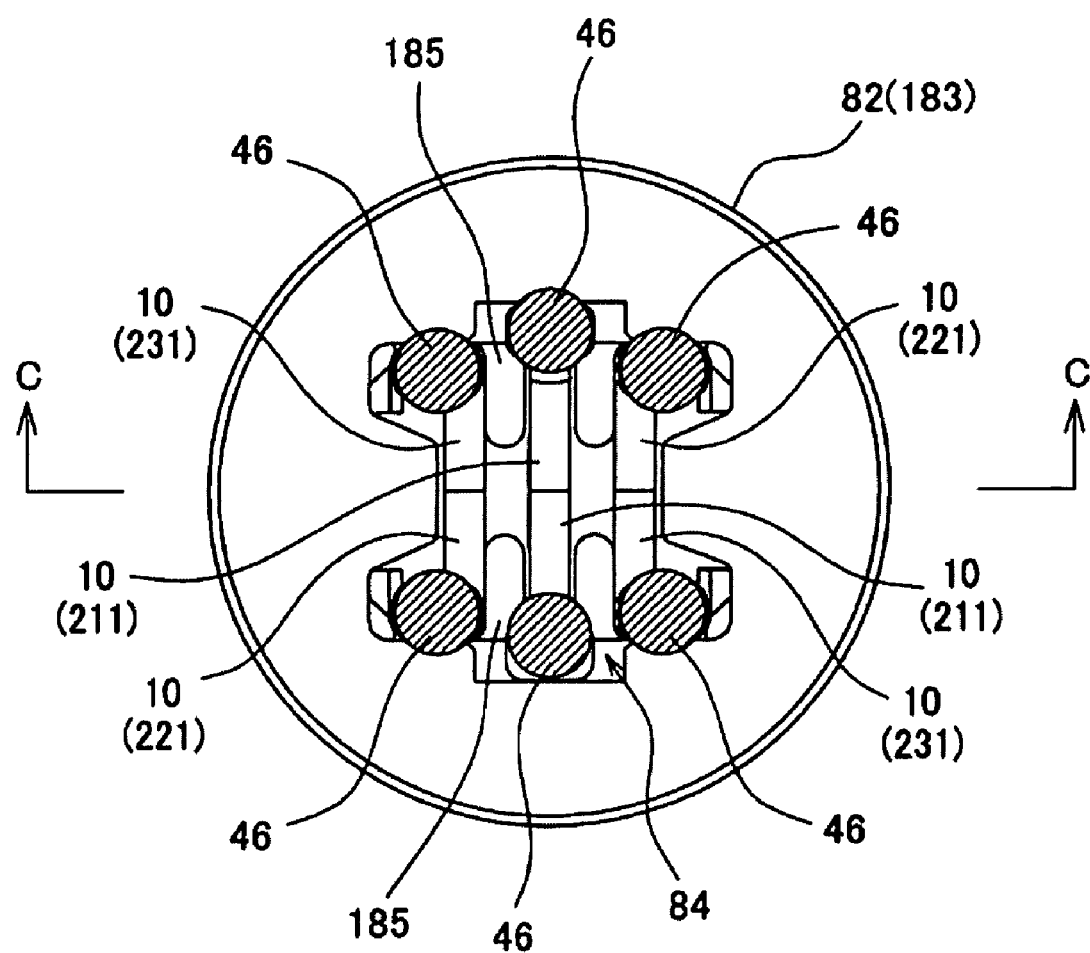
FIG. 17 is a plan view of the insulating separator in a state in which the leadframes are arranged in the element insertion hole.
Figure 18:
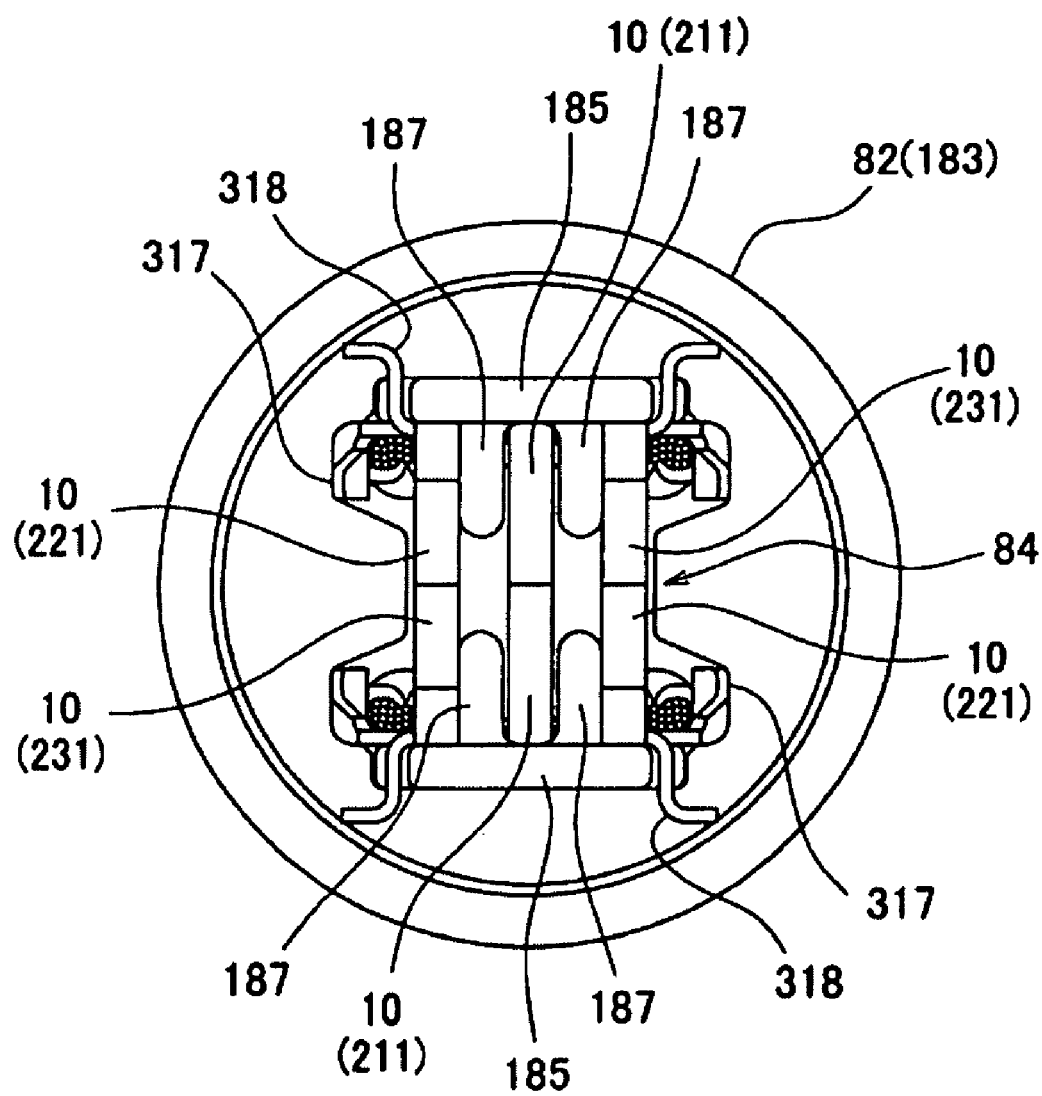
FIG. 18 is a bottom view of the insulating separator in a state in which the leadframes are arranged in the element insertion hole.
Figure 19:
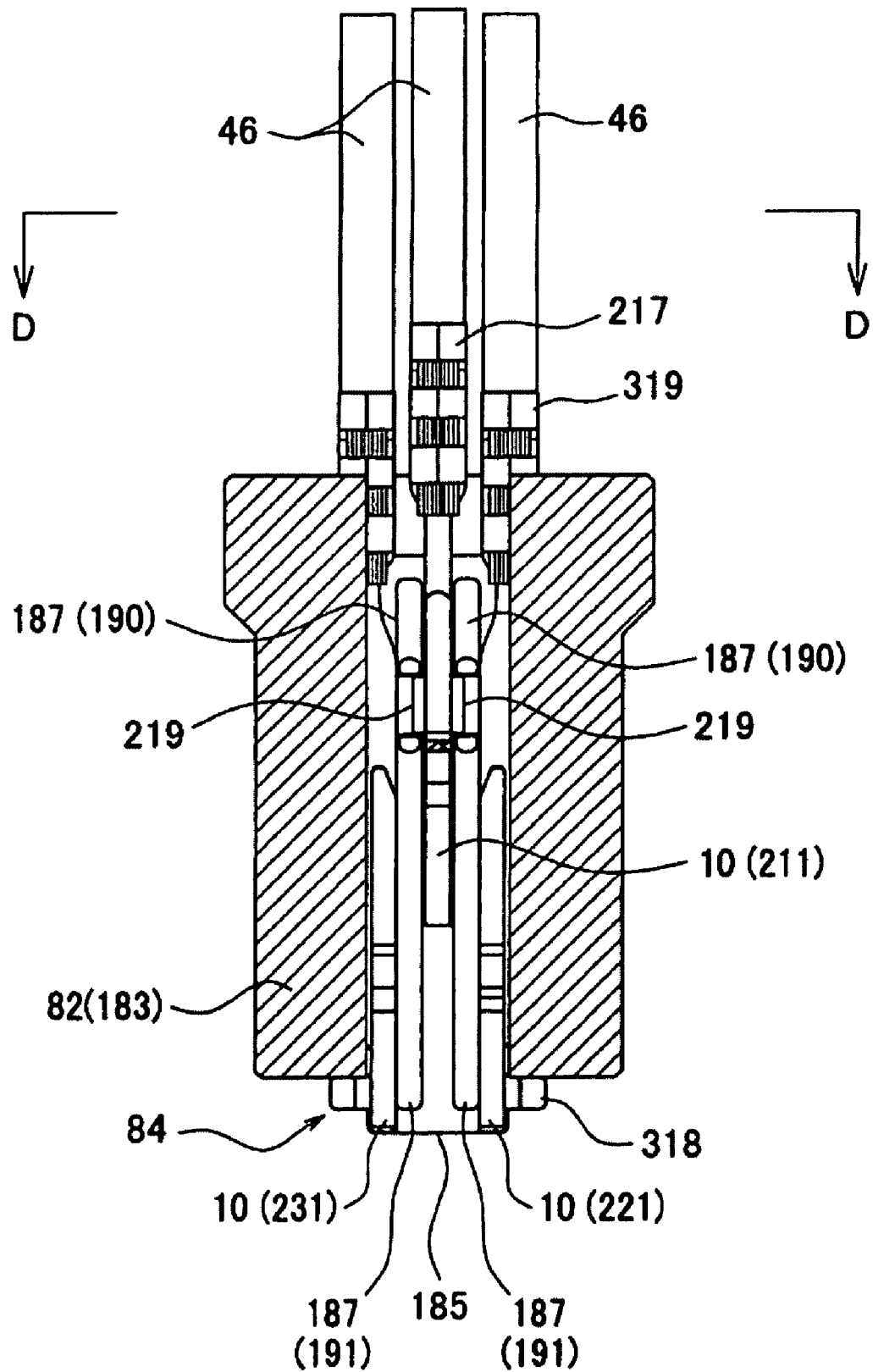
FIG. 19 is a cross-sectional view, taken along line C-C in FIG. 17, of the insulating separator.

Concerning the insulating separator 82 in the state in which the leadframes 10 are arranged in the element insertion hole 84, a plan view is shown in FIG. 17, a bottom view is shown in FIG. 18, and a cross-sectional view taken along line C-C in FIG. 17 is shown in FIG. 19. In FIG. 17, the lead wires 46 are shown as a cross-sectional view taken along line D-D in FIG. 19.

As shown in FIGS. 17 and 18, the six leadframes 10 are arranged by threes so as to be divided into two regions (a region opposing the electrode terminal portions 30, 31 and 32 of the detecting element and a region opposing the electrode terminal portions 34, 35 and 36). Further, the leadframes 10 are arranged in the element insertion hole 84 of the insulating separator 82 in a state in which the element abutting portions (the element abutting portion 216 and the element abutting portion 315) of the opposing leadframes 10 abut against one another.

In addition, as shown in FIG. 19, the partition walls 187 of the inner separator 185 prevent the three adjacent leadframes 10 (the first leadframe 211, the second leadframe 221, and the third leadframe 231) from coming into contact with one another.

As the rear end portion of the detecting element 4 is inserted into the element insertion hole 84 of the insulating separator 82 in the state in which the leadframes 10 are thus arranged, the element abutting portions (the element abutting portion 216 and the element abutting portion 315) of the leadframes 10 and the electrode terminal portions 30, 31, 32, 34, 35 and 36 of the detecting element 4 abut and electrically connect to one another.

In addition, of the three leadframes 10, two adjacent leadframes 10 (e.g., two including the first leadframes 211 and 221 or two including the first leadframes 211 and 231) are arranged such that their axial arrangement positions are different from one another.

Of the plurality of electrode terminal portions, two adjacent electrode terminal portions in the same plane of the detecting element 4 (e.g., two including the electrode terminal portions 30 and 31, two including the electrode terminal portions 31 and 32, two including the electrode terminal portions 34 and 35, and two including the electrode terminal portions 35 and 36) respectively have different axial forming positions. Further, the leadframes 10 are respectively arranged at positions where they are connected to the electrode terminal portions 30, 31, 32, 34, 35 and 36. As a result, the two adjacent leadframes 10 are arranged such that their axial arrangement positions are mutually different.

It should be noted that the assembly operation for integrally assembling the detecting element 4, the leadframes 10, and the insulating separator 82 is executed in an interim stage of the process of manufacturing the $NO_x$ sensor 2. Further, in the process of manufacturing the $NO_x$ sensor 2, the assembly operation of an intermediate assembly 105 comprising the detecting element 4, the ceramic sleeve 6, the talc ring 108, the ceramic holder 106, and the metal shell 102 is executed in a preliminary stage of this assembly operation.

Figure 20:
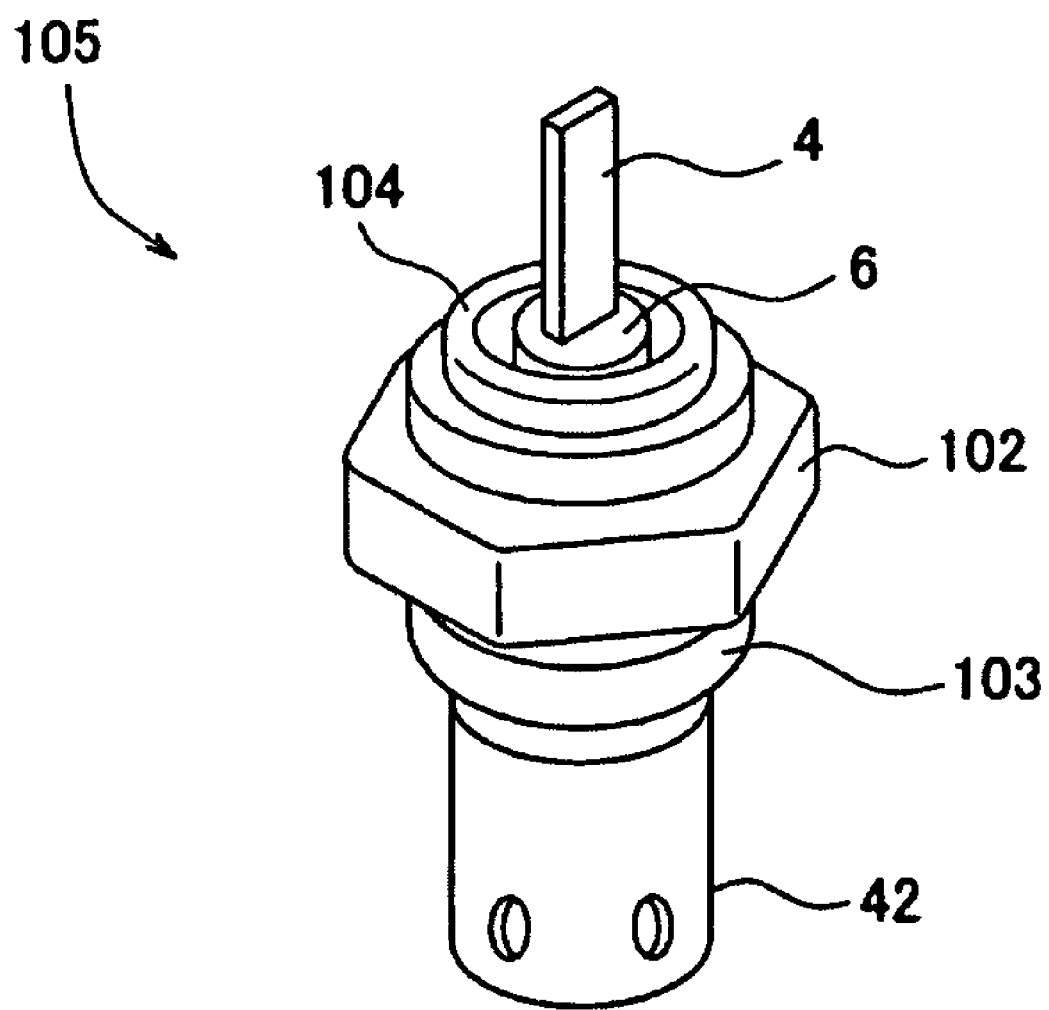
FIG. 20 is a perspective view of an intermediate assembly in a state in which a rear end side of the detecting element protrudes from a rear end portion of a metal shell and a rear end portion of a ceramic sleeve.

FIG. 20 shows a perspective view of the intermediate assembly 105 in a state in which the rear end side of the detecting element 4 protrudes from the rear end portion 104 of the metal shell 102 and the rear end portion of the ceramic sleeve 6. In the process of manufacturing the $NO_x$ sensor 2, the leadframes 10, the insulating separator 82 and the detecting element 4 can be integrally assembled by inserting the detecting element 4 (as part of the intermediate assembly 105) into the element insertion hole 84 of the insulating separator 82.

After the leadframes 10, the insulating separator 82 and the detecting element 4 are integrally assembled, the outer cylinder 44 and the like are joined to the metal shell 102 by laser welding or the like. Also, a fixing operation for fixing the grommet 50 to the outer cylinder 44 by crimping is executed to thereby complete the $NO_x$ sensor 2, which ends the process of manufacturing the $NO_x$ sensor 2.

In this embodiment, the $NO_x$ sensor 2 corresponds to the claimed sensor, the leadframe 10 corresponds to the metallic terminal member, the recessed portions of the element insertion hole 84 of the outer separator 183 correspond to the recessed portions in the outer separator, and the partition walls 187 (the rear end partition walls 190 and the leading end partition walls 191) correspond to the partition walls.

In addition, the position determining portion 184 of the outer separator 183 corresponds to the position determining portion, the rear end partition wall 190 and the leading end partition wall 191 correspond to the partition walls, the frame retaining portion 219 of the first leadframe corresponds to a projecting portion of the metallic terminal member, and the terminal retaining portions 318 of the second leadframe 221 and the third leadframe 231 correspond to the leading-end engaging portions.

As described above, in the $NO_x$ sensor 2 of this embodiment, the insulating separator 82 is not configured as consisting of a single member but configured by including the outer separator 183 and the inner separators 185.

Further, in this insulating separator 82, the partition walls 187 for mutually insulating the leadframes 10 are formed not on the outer separator 183 having the element insertion hole 84 but on the inner separators 185 which are provided as separate members from the outer separator 183.

By using the insulating separator 82 having such a configuration, as to the leadframes 10 (first leadframes 211) whose positioning in the element insertion hole 84 is otherwise difficult, the leadframes 10 together with the inner separators 185 can be inserted into the element insertion hole 84 of the outer separator 183.

Namely, in the preliminary stage before inserting the leadframe 10 (first leadframe 211) into the element insertion hole 84, the leadframe 10 is arranged on the inner separator 185 which is a part of the insulating separator 82, so that the relative position between the inner separator 185 and the leadframe 10 can be set in a directly visually confirmable manner.

Since the relevant members are directly visible, the relative position between the inner separator 185 and the leadframe 10 can be easily set to a particular position.

As a result, when the leadframe 10 together with the inner separator 185 is inserted into the element insertion hole 84 of the outer separator 183, the relative position between the inner separator 185 and the outer separator 183 can be easily set to a particular position, and the operation of positioning the leadframe 10 in the element insertion hole 84 of the insulating separator 82 is facilitated. Namely, the leadframe 10 can be easily arranged with respect to a target position in the element insertion hole 84.

Hence, according to the $NO_x$ sensor 2 of this embodiment, even in the sensor provided with the insulating separator 82 having the element insertion hole 84, the leadframes 10 can easily be arranged at appropriate positions in arranging the leadframes 10 in the element insertion hole 84.

The insulating separator 82 of this embodiment is provided with a pair of inner separators 185, and the pair of inner separators 185 are respectively arranged on the first plate surface 21 and the second plate surface 23 between the plate surfaces of the detecting element 4.

Thus, since a pair of inner separators 185 are provided, even in the case where the leadframes 10, whose arrangement is otherwise not easy, are respectively present on the obverse plate surface and the reverse plate surface between the plate surfaces of the detecting element 4, the leadframes 10 can be arranged appropriately on the obverse plate surface and the reverse plate surface of the detecting element 4.

In addition, the outer separator 183 of this embodiment is provided with a pair of position determining portions 184 each provided in the arrangement region (recessed portion 195) of the inner separator 185 in the element insertion hole 84 and adapted to abut against the rear end portion 189 (rear opposing face) of the inner separator 185.

In other words, since the outer separator 183 is provided with the position determining portions 184, the outer separator 183 is capable of limiting the moving range (specifically, the moving range in the direction toward the rear end) of the inner separators 185 inside the element insertion hole 84.

Further, the position where the position determining portion 184 is formed is set in advance so that the position where the inner separator 185 is arranged in the element insertion hole 84 coincides with a target position, and the rear end portion 189 of the inner separator 185 abuts against the position determining portion 184 when the inner separator 185 is inserted into the element insertion hole 84. Consequently, the positioning operation at the time of arranging the inner separator 185 in the element insertion hole 84 is facilitated.

Thus, since the positioning operation at the time of arranging the inner separator 185 in the element insertion hole 84 is facilitated, it is possible to alleviate problems encountered in the positioning operation when the leadframes 10 and the inner separators 185 are arranged in the element insertion hole 84, thereby facilitating the operation of positioning the leadframes 10 in the element insertion hole 84.

In addition, the inner separator 185 has the rear end partition walls 190 and the leading end partition walls 191 which abut against the frame retaining portions 219 of the leadframe 10 (first leadframe 211).

Since the inner separator 185 has the rear end partition walls 190 and the leading end partition walls 191, if the leadframe 10 (first leadframe 211) tends to move in the axial direction (in the direction toward the rear end or the leading end), each rear end partition wall 190 or each leading end partition wall 191 abuts against the rear opposing face or the leading opposing face of the frame retaining portion 219 to limit the moving range of the leadframe 10.

The rear opposing face is a surface facing the rear side (rear end side), while the leading opposing face is a surface facing the leading side (leading end side).

As a result, the axial positioning of the leadframe 10 (first leadframe 211) with respect to the inner separator 185 is facilitated, and it is possible to suppress the occurrence of an offset in the relative axial position between the leadframe 10 and the inner separator 185.

Therefore, according to this embodiment, in arranging the leadframes 10 in the element insertion hole 84 of the insulating separator 82, the problems encountered in the operation of relatively positioning the inner separator 185 and the leadframe 10 are alleviated, so that it becomes possible to easily arrange the leadframes 10 at appropriate positions.

In this embodiment, the rear end partition walls 190 and the leading end partition walls 191 provided on the inner separator 185 are respectively arranged to abut against the first retaining surfaces 235 (rear opposing faces) and the second retaining surfaces 237 (leading opposing faces) of the frame retaining portions 219.

Namely, the inner separator 185 has the rear end partition walls 190 and the leading end partition walls 191 so as to abut not only one of the first retaining surfaces 235 (rear opposing faces) and the second retaining surfaces 237 (leading opposing faces) of the frame retaining portions 219 but both of the first retaining surfaces 235 (rear opposing faces) and the second retaining surfaces 237 (leading opposing faces).

Consequently, the inner separator 185 is capable of limiting movement in both axial directions (in the directions toward the leading end side and the rear end side) of the leadframe 10.

Therefore, according to this embodiment, in arranging the leadframe 10 in the element insertion hole 84 of the insulating separator 82, since movement of the leadframe 10 can be limited in both axial directions, operation of the relative positioning between the inner separator 185 and the leadframe 10 can be further facilitated.

In addition, in this embodiment, of the leadframes 10, each of the second leadframe 221 and the third leadframe 231 has a terminal retaining portion 318 which engages the leading end face of the insulating separator 82.

Thus, since the leadframe 10 has the terminal retaining portion 318, it becomes possible to easily determine the relative position between the leading end face of the insulating separator 82 and the leadframe 10, thereby facilitating the axial positioning between the leadframe 10 and the insulating separator 82.

Particularly when the leadframe 10 is inserted into the element insertion hole 84 of the insulating separator 82, the metallic terminal member is inserted until the terminal retaining portion 318 abuts the leading end face of the insulating separator 82, thereby making it possible to easily set the arrangement position of the metallic terminal member in the element insertion hole to a particular position.

As a result, in arranging the leadframe 10 in the element insertion hole 84 of the insulating separator 82, the extent of insertion of the leadframe 10 (the second leadframe 221 and the third leadframe 231) into the element insertion hole 84 can be determined by determining whether or not the terminal retaining portion 318 abuts against the leading end face of the insulating separator 82.

Therefore, according to this embodiment, since the extent of insertion of the leadframe 10 (the second leadframe 221 and the third leadframe 231) into the element insertion hole 84 can be easily determined, the operation of relatively positioning the insulating separator 82 and the leadframe 10 is further facilitated.

In addition, an arrangement provided is such that the leadframe 10 has a frame body portion 212 or 312 and the element abutting portion 216 or 315, while the inner separator 185 has a plate-shaped body portion 186 of a plate shape adapted to abut against the frame body portion 212 or 312.

In other words, since the inner separator 185 has a plate-shaped body portion 186, the arrangement position of the leadframe 10 relative to the inner separator 185 can be easily set to a particular position in a preliminary stage before inserting the leadframe 10 into the element insertion hole 84. This facilitates the operation of positioning the leadframes 10 in the element insertion hole 84 of the insulating separator 82.

In addition, the leadframe 10 (first leadframe 211) has a connecting portion 214, so that when the detecting element 4 is inserted into the element insertion hole 84 with the leadframe 10 arranged therein, an external force applied by the detecting element 4 can be absorbed because the connecting portion 214 is elastically deformed.

As a result, when the detecting element 4 is inserted into the element insertion hole 84, it is possible to prevent the arrangement position of the leadframe 10 from moving due to external force from the detecting element 4.

In addition, the outer separator 183 has a pair of recessed portions 195 formed in the element insertion hole 84 and serving as the regions where the inner separators 185 are disposed. Further, the plate-shaped body portion 186 of the inner separator 185 is arranged so as to be disposed in the recessed portion 195 by sliding from the leading end side of the outer separator 183 toward the rear end side along the inner surface of the element insertion hole 84.

Thus, since the outer separator is provided with a pair of recessed portions 195, when the inner separators 185 are inserted (slid) into the element insertion hole 84 of the outer separator 183, it is possible to easily set the arrangement positions of the inner separators 185 in the element insertion hole 84.

In the sensor having the outer separator 183 and the inner separators 185 constructed as described above, the operation of positioning the leadframes 10 in the element insertion hole 84 of the insulating separator 82 is further facilitated.

In addition, in the $NO_x$ sensor 2 of this embodiment, of the plurality of electrode terminal portions 30, 31, 32, 34, 35 and 36, two adjacent electrode terminal portions in the same plane of the detecting element 4 respectively have different axial forming positions. Further, the plurality of leadframes 10 are respectively arranged at positions where they are connected to the electrode terminal portions 30, 31, 32, 34, 35 and 36.

The $NO_x$ sensor 2 having such a construction makes it possible to secure a large distance between two adjacent ones of the electrode terminal portions and to secure a large distance also between the two leadframes 10 which are connected to these two electrode terminal portions.

Therefore, according to the $NO_x$ sensor 2 of this embodiment, it is possible to ensure insulation between two adjacent electrode terminal portions and to secure insulation between the leadframes 10 which are connected to these electrode terminal portions.

Furthermore, in the $NO_x$ sensor 2 of this embodiment, the electrode terminal portions 30, 31 and 32 formed on the first plate surface 21 of the detecting element 4 and the electrode terminal portions formed on the second plate surface 23 of the detecting element 4 are arranged plane-symmetrically about the detecting element 4.

Thus, in the case where the plurality of electrode terminal portions 30, 31, 32, 34, 35 and 36 are arranged plane-symmetrically on the first plane surface 21 and the second plane surface 23 of the detecting element 4, the plurality of leadframes 10 are also arranged substantially plane-symmetrically. As a result, the state of distribution of pressure applied from the plurality of leadframes 10 to the detecting element 4 becomes substantially similar on the first plate surface 21 and the second plate surface 23 of the detecting element 4.

Consequently, it becomes possible to prevent nonuniform contact between the detecting element 4 and the plurality of leadframes 10 and between the first plate surface 21 and the second plate surface 23 of the detecting element 4, and to render satisfactory contact between, on the one hand, the leadframes 10 and, on the other hand, corresponding ones of the electrode terminal portions 30, 31, 32, 34, 35 and 36.

Although a description of an embodiment of the invention has been given above, the invention is not limited thereto and it is possible for the invention to adopt various forms.

For example, although in the above-described embodiment the insulating separator 82 has two inner separators 185, the number of inner separators is not limited to two and may be singular or three or more in correspondence with the state of arrangement of the metallic terminal members (leadframes).

In addition, although a pair of notched portions 188 are formed in the inner separator 185 as portions against which the respective terminal retaining portion 318 (leading end engaging portion) of the leadframe 10 (metallic terminal member) abut, it is possible to use an insulating separator which does not have notched portions.

For example, even in a case where the insulating separator does not have notched portions, if the metallic terminal member and the insulating separator are configured such that the leading end engaging portion of the metallic terminal member abuts against the leading end face of the inner separator or the leading end face of the contact body portion, it is possible to easily determine the relative position between the metallic terminal member and the insulating separator.

The portion of the leading end face of the insulating separator with which the leading end engaging portion of the metallic terminal member engages may be either the leading end face of the outer separator or the leading end face of the inner separator, or may be both leading end faces of the outer separator and the inner separator.

In addition, the sensor in accordance with the invention is not limited to a form in which the metallic terminal members are inserted into the element insertion hole after all of the metallic terminal members are arranged on the inner separator. For example, an arrangement may be provided such that after one or some of the plurality of metallic terminal members are arranged on the inner separator and are inserted into the element insertion hole, the remaining metallic terminal members are subsequently arranged in the element insertion hole.

In addition, the electrode terminal portions which are formed on the obverse plate surface and the reverse plate surface of the detecting element are not limited to those in which a plurality of electrode terminal portions are formed on the obverse plate surface and the reverse plate surface, respectively. For example, it is possible to adopt a form in which a plurality of obverse plate surfaces (or reverse plate surfaces) are formed, and a single reverse plate surface (or obverse plate surface) is formed.

Furthermore, although a double protector (the outer protector 42 and the inner protector 43) is provided as a protector for covering the protruding portion of the detecting element 4 and having a plurality of holes, the protector is not limited to a double structure, and the protector may have a single structure or a triple or more structure.

In addition, the hole portions provided in the protector are not limited to the forming positions and number as in the above-described embodiment. As for the forming positions of the hole portions, for example, the hole portions may be absent in a rear end-side region of the side wall portion of the inner protector 43 (i.e., a region close to the detecting element 4), and the hole portions may be provided in a leading end-side region thereof. The leading end-side region in this case be a side wall portion of the protector, or a leading end face portion of the protector.

In addition, although in the above-described embodiment the outer separator 183 of the insulating separator 82 is formed by a single member, it is possible to adopt a form in which the outer separator 183 is formed by a plurality of members which are divided in a cross section along line A-A or line B-B in FIG. 6. Namely, the outer separator may be configured to have a plurality of members sandwiching the detecting element and the metallic terminal members.

Furthermore, the metallic terminal member (leadframe 10) having a projecting portion is not limited to the first leadframe 211 having the pair of frame retaining portions 219 as shown in FIG. 12, and may be configured such that the projecting portion is formed at a leading end side.

Figure 22:
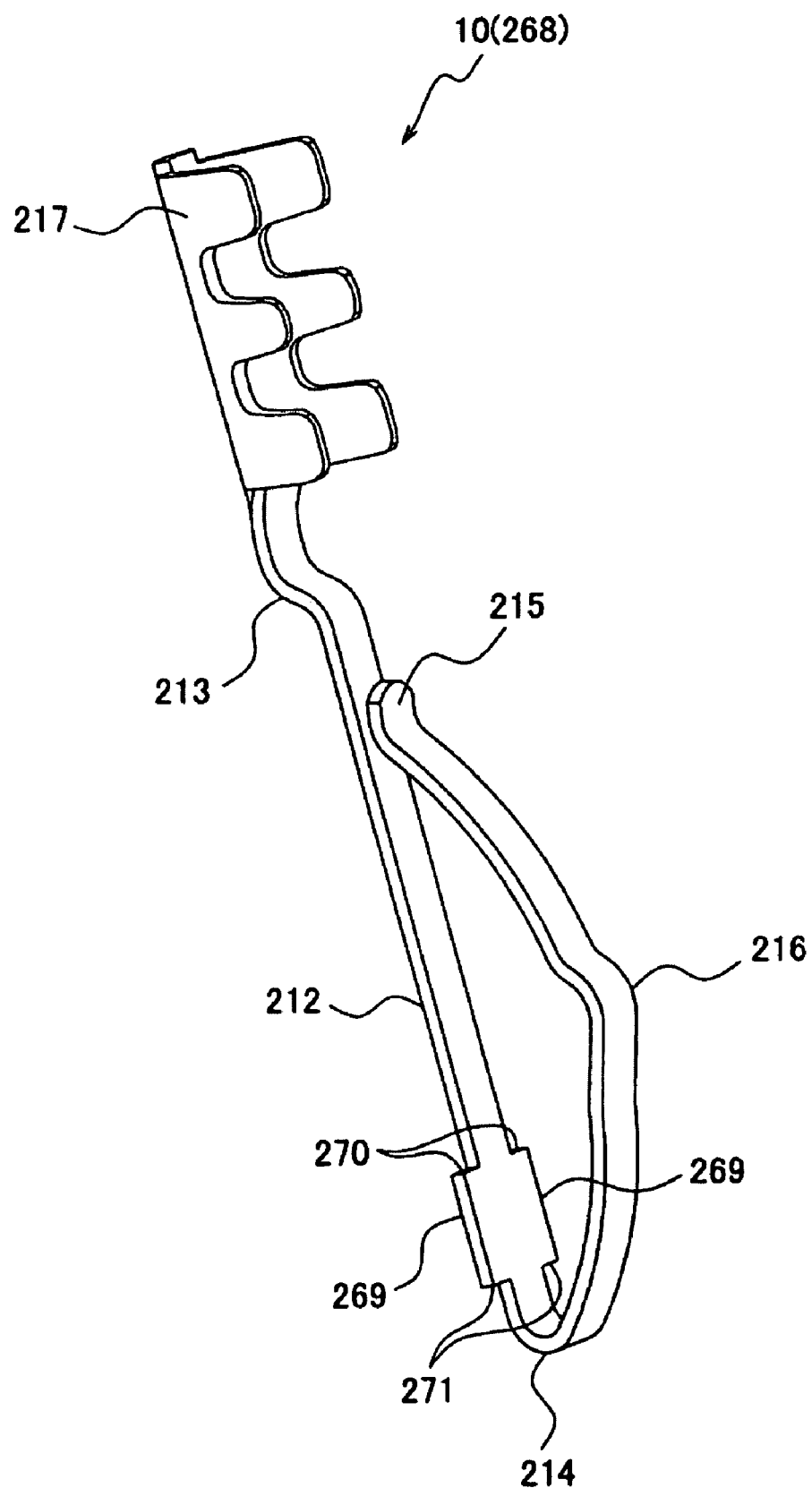
FIG. 22 is a perspective view of a modified first leadframe.
Figure 23:
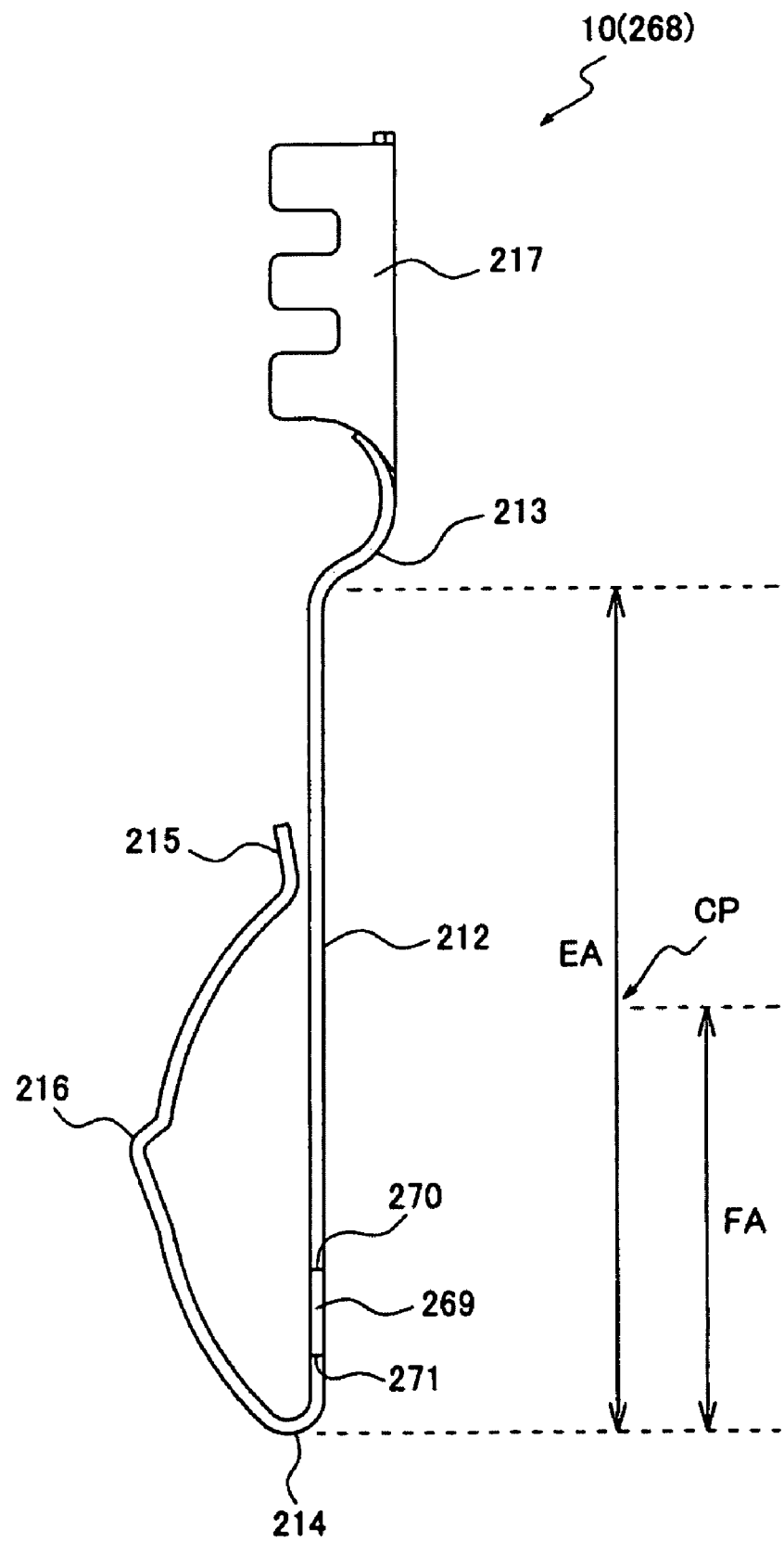
FIG. 23 is a side elevational view of the modified first leadframe.

Accordingly, as a modification, a description will be given of a modified first leadframe 268 having the projecting portion formed on a leading end side thereof. FIG. 22 shows a perspective view of the modified first leadframe 268, and FIG. 23 shows a side elevational view of the modified first leadframe 268.

The modified first leadframe 268 is configured such that if a portion thereof surrounded by the insulating separator is assumed to be a surrounded region EA, a pair of projecting portions 269 are formed in a region FA located closer to the leading end side than an axially central position CP of the surrounded region EA. Further, each of the projecting portions 269 has a first retaining surface 270 opposing the axial rear end side of the frame body portion 212 and a second retaining surface 271 opposing the axial leading end side of the frame body portion 212. In the modified first leadframe 268, component elements similar to those of the first leadframe 211 are denoted by the same reference numerals.

Figure 21:
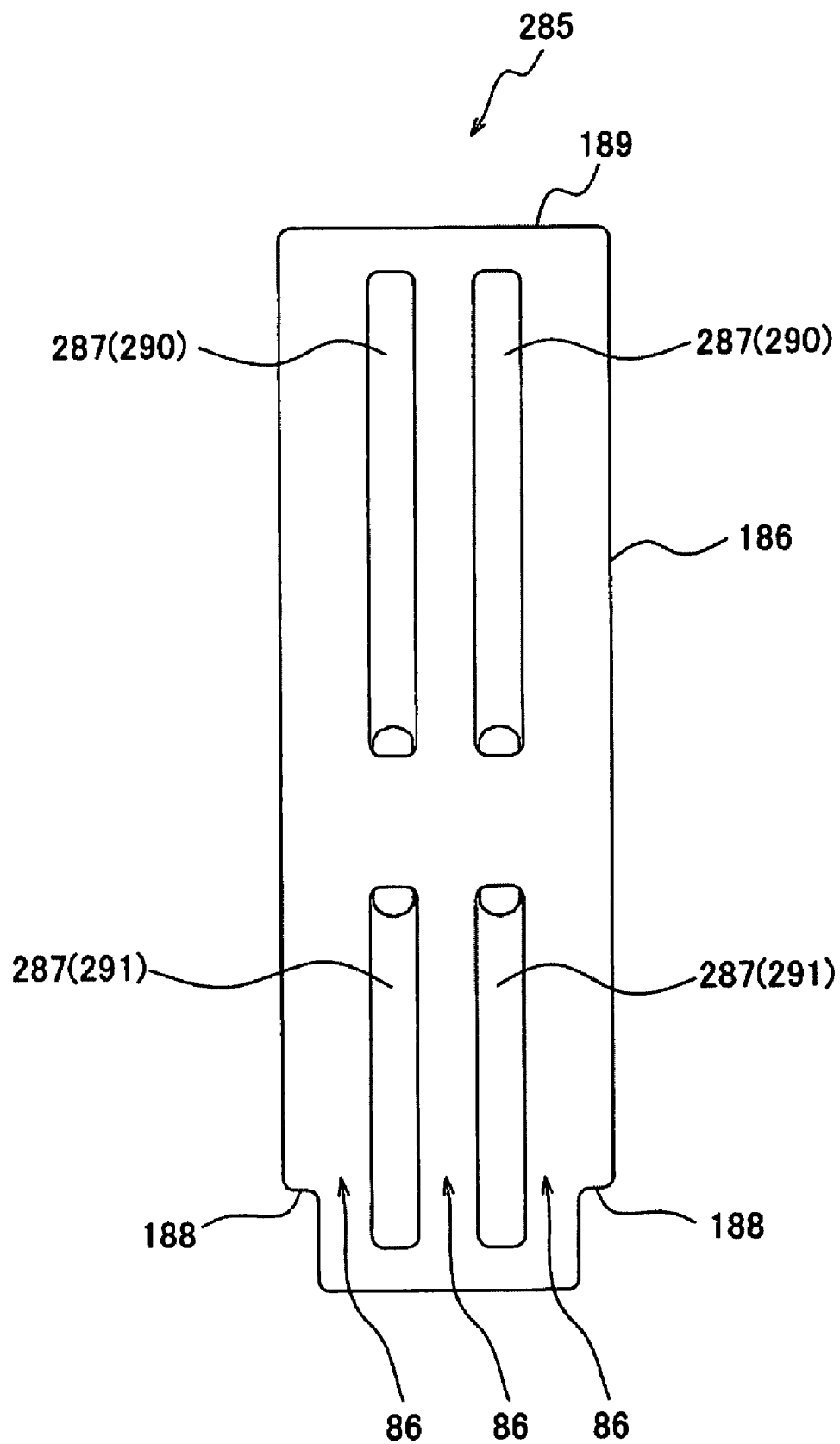
FIG. 21 is a front elevational view of a modified inner separator.

In addition, as the inner separator corresponding to this modified first leadframe 268, it is possible to cite a modified inner separator 285 such as the one shown in FIG. 21.

As partition walls for mutually insulating the plurality of metallic terminal members, this modified inner separator 285 is provided with partition walls 287 including two rear end partition walls 290 formed on the rear end side (upper side in FIG. 21) and two leading end partition walls 291 formed on the leading end side (lower side in FIG. 21). Further, the modified inner separator 285 is so configured that each projecting portion 269 of the modified first leadframe 268 is disposed in a gap region between the rear end partition wall 290 and the leading end partition wall 291.

Namely, the modified inner separator 285 is configured in a form in which the gap region between the rear end partition wall 290 and the leading end partition wall 291 is located closer to the leading end side than the gap region between the rear end partition wall 190 and the leading end partition wall 191 in the inner separator 185. In the modified inner separator 285, component elements similar to those of the inner separator 185 are denoted by the same reference numerals.

The positioning of the leading end side in the surrounded region EA of the modified first leadframe 268 is facilitated by causing the projecting portion 269 and the partition wall 287 to abut against each other using the above-described modified first leadframe 268 and modified inner separator 285.

In the case where the outer separator having the element insertion hole is used, there are cases where after the modified first leadframe 268 together with the modified inner separator 285 is arranged in the element insertion hole, the operation of inserting the detecting element from the leading end side of the element insertion hole is carried out. In such a case, by using the modified first leadframe 268 in which the projecting portions 269 are formed closer to the leading end side than the axially central position CP of the surrounded region EA, even if an external force is applied to the modified first leadframe 268 accompanying the inserting operation of the detecting element, it is possible to suppress movement of the modified first leadframe 268 to a misaligned position.

It should further be apparent to those skilled in the art that various changes in form and detail of the invention as shown and described above may be made. It is intended that such changes be included within the spirit and scope of the claims appended hereto.

This application is based on Japanese Patent Application JP 2007-6329, filed Jan. 15, 2007, and Japanese Patent Application JP 2007-313680, filed Dec. 4, 2007, the entire contents of which are hereby incorporated by reference, the same as if set forth at length.

What is claimed is:

1. A sensor comprising:
a detecting element having a plate-like shape extending in an axial direction and whose leading end side is directed toward a gas to be measured, and a plurality of electrode terminal portions formed on at least one of an obverse plate surface and a reverse plate surface of a rear end side of the detecting element;
a plurality of metallic terminal members for electrically connecting an external device and the electrode terminal portions of the detecting element; and
an insulating separator in which the electrode terminal portions of the detecting element and the metallic terminal members are connected with one another,
wherein the insulating separator comprises:
an outer separator which surrounds the electrode terminal portions of the detecting element and the metallic terminal members; and
an inner separator at least a portion of which is disposed radially inwardly of the outer separator and which has partition walls for positioning respective ones of the plurality of metallic terminal members and for insulating the plurality of metallic terminal members from one another.

2. The sensor according to claim 1, wherein the outer separator has a cylindrical shape and has an element insertion hole penetrating therethrough in the axial direction, and at least a portion of the inner separator is disposed inside the element insertion hole.

3. The sensor according to claim 2, wherein at least one of the plurality of metallic terminal members has a projecting portion projecting perpendicularly to the axial direction, and at least one of the partition walls abuts against the projecting portion to effect positioning of the metallic terminal member in the axial direction.

4. The sensor according to claim 3, wherein the metallic terminal member has a surrounded region surrounded by the insulating separator, and the projecting portion is provided closer to a leading end side than an axially central position of the surrounded region.

5. The sensor according to claim 1, wherein at least one of the plurality of metallic terminal members has a leading end engaging portion which engages a leading end face of the insulating separator.

6. The sensor according to claim 1, wherein at least one of the plurality of metallic terminal members has a frame body portion of an elongated shape extending in the axial direction and an element abutting portion which extends from a leading end side of the frame body portion such that at least a portion thereof is disposed between the frame body portion and the detecting element, and which element abutting portion abuts against an electrode terminal portion of the detecting element, and wherein the inner separator has a plate-shaped body portion adapted to abut against the frame body portion.

7. The sensor according to claim 6, wherein the element abutting portion has a connecting portion which is connected to a leading end of the frame body portion, and at least a portion of the connecting portion is adapted to undergo elastic deformation upon application of an external force thereto by the detecting element.

8. The sensor according to claim 6, wherein the outer separator has a recessed portion for receiving the plate-shaped body portion of the inner separator, and the plate-shaped body portion of the inner separator is disposed in the recessed portion by sliding from a leading end side of the outer separator toward a rear end side along an inner surface of the outer separator.

9. The sensor according to claim 8, wherein the outer separator has on a rear end side of the recessed portion a position determining portion which effects positioning of the inner separator in the axial direction inside the outer separator by abutting against the plate-shaped body portion of the inner separator.

10. The sensor according to claim 1, wherein, of the plurality of electrode terminal portions, two adjacent ones of the electrode terminal portions in a same plane of the detecting element are formed at different axial positions, and individual ones of the plurality of metallic terminal members are arranged so as to connect to corresponding ones of the electrode terminal portions.

11. The sensor according to claim 1, wherein the detecting element has a plurality of electrode terminal portions formed on an obverse plate surface and a reverse plate surface, respectively, on the rear end side, and a pair of inner separators are provided as the inner separator and are respectively arranged on the obverse plate surface and the reverse plate surface of the detecting element.

12. The sensor according to claim 11, wherein, of the plurality of electrode terminal portions, the electrode terminal portions which are formed on the obverse plate surface of the detecting element and the electrode terminal portions which are formed on the reverse plate surface of the detecting element are arranged plane-symmetrically about the detecting element.

13. A sensor comprising:
a detecting element which has a plate-like shape extending in an axial direction and whose leading end side is directed toward a gas to be measured, and a plurality of electrode terminal portions formed on at least one of an obverse plate surface and a reverse plate surface of a rear end side of the detecting element;
a plurality of metallic terminal members for electrically connecting an external device and the electrode terminal portions of the detecting element; and
an insulating separator in which the electrode terminal portions of the detecting element and the metallic terminal members are connected with one another,
wherein at least one of the plurality of metallic terminal members comprises a frame body portion of an elongated shape extending in the axial direction and an element abutting portion which extends from a leading end side of the frame body portion such that at least a portion thereof is disposed between the frame body portion and the detecting element, and which element abutting portion abuts against an electrode terminal portion of the detecting element, the element abutting portion having a connecting portion which is connected to a leading end of the frame body portion, and at least a portion of the connecting portion is adapted to undergo elastic deformation upon application of an external force thereto by the detecting element,
wherein, of the plurality of electrode terminal portions, two adjacent ones of the electrode terminal portions in a same plane of the detecting element are formed at different axial positions, and
wherein respective axial arrangement positions of the plurality of metallic terminal members are set so as to connect individual ones of the plurality of metallic terminal members with corresponding ones of the electrode terminal portions.

14. The sensor according to claim 13, wherein the detecting element has a plurality of electrode terminal portions formed on an obverse plate surface and a reverse plate surface, respectively, on the rear end side, and, of the plurality of electrode terminal portions, the electrode terminal portions which are formed on the obverse plate surface of the detecting element and the electrode terminal portions which are formed on the reverse plate surface of the detecting element are arranged plane-symmetrically about the detecting element.

* * * * *